US012589206B2

(12) United States Patent
Chang et al.

(10) Patent No.: US 12,589,206 B2
(45) Date of Patent: Mar. 31, 2026

(54) MEDICAL INJECTION SYSTEM

(71) Applicant: SOLTEAM INCORPORATION,
Taoyuan (TW)

(72) Inventors: Chun-Yun Chang, Taoyuan (TW);
Yeong-Lii Lin, Taoyuan (TW);
Ping-Lung Lee, Taoyuan (TW);
Frederic Delort, Taoyuan (TW);
Chung-Yu Chen, Taoyuan (TW);
Jung-Lan Huang, Taoyuan (TW)

(73) Assignee: SOLTEAM INCORPORATION,
Taoyuan (TW)

( * ) Notice: Subject to any disclaimer, the term of this
patent is extended or adjusted under 35
U.S.C. 154(b) by 636 days.

(21) Appl. No.: 18/185,821

(22) Filed: Mar. 17, 2023

(65) Prior Publication Data

US 2024/0307619 A1      Sep. 19, 2024

(51) Int. Cl.
A61M 5/20       (2006.01)
A61M 5/32       (2006.01)

(52) U.S. Cl.
CPC ........... A61M 5/20 (2013.01); A61M 5/3204
(2013.01); A61M 2005/206 (2013.01)

(58) Field of Classification Search
CPC .................. A61M 5/20; A61M 5/3204; A61M
2005/206; A61M 5/3202; A61M 5/31576;
A61M 2205/581; A61M 2205/27; A61M
2205/43; A61M 2205/8281; A61M
2210/04
See application file for complete search history.

(56) References Cited

U.S. PATENT DOCUMENTS

| | | | |
|---|---|---|---|
| 2013/0046246 A1* | 2/2013 | Cross ................... | A61M 5/3272 |
| | | | 604/189 |
| 2016/0008541 A1* | 1/2016 | Hirschel ................. | A61M 5/24 |
| | | | 604/137 |
| 2017/0136189 A1* | 5/2017 | Tschirren ........... | A61M 5/3156 |
| 2019/0266921 A1* | 8/2019 | Chang ................... | G09B 23/285 |
| 2021/0093789 A1* | 4/2021 | Plambech ........... | A61M 5/2033 |
| 2021/0113776 A1* | 4/2021 | Hopkins .............. | G09B 23/285 |
| 2021/0162133 A1* | 6/2021 | Dasbach ............. | A61M 5/2033 |
| 2022/0387719 A1* | 12/2022 | Wang ...................... | A61M 5/20 |
| 2023/0008831 A1* | 1/2023 | Huang .................... | A61M 5/20 |
| 2024/0207518 A1* | 6/2024 | Franke .................... | A61M 5/20 |

(Continued)

FOREIGN PATENT DOCUMENTS

| | | |
|---|---|---|
| CN | 108136121 A | 6/2018 |
| CN | 109641102 A | 4/2019 |

(Continued)

*Primary Examiner* — Michael J Tsai
*Assistant Examiner* — Zachariah K Whitrock
(74) *Attorney, Agent, or Firm* — ScienBiziP, P.C.

(57) ABSTRACT

A medical injection system is provided. The medical injection system includes an injection initiation feedback module. The injection initiation feedback module includes an actuator and a click collar, which comprise an impact plate and a click surface, respectively. The click collar further includes a click surface protrusion to restrict the click surface from contacting the impact plate. The actuator further includes an impact plate groove to accommodate the click surface protrusion at the initiation of injection and the click surface contacts the impact plate to generate an injection initiation feedback prompt.

10 Claims, 15 Drawing Sheets

150

(56)     References Cited

U.S. PATENT DOCUMENTS

| | | | |
|---|---|---|---|
| 2024/0277936 A1* | 8/2024 | Boström | ................ A61M 5/178 |
| 2024/0416041 A1* | 12/2024 | Shetty | ................. A61M 5/2053 |
| 2025/0345520 A1* | 11/2025 | Säll | ......................... A61M 5/20 |

FOREIGN PATENT DOCUMENTS

| | | | |
|---|---|---|---|
| CN | 113209421 A | 8/2021 |
| CN | 214807465 U | 11/2021 |
| CN | 111558109 B | 2/2022 |
| EP | 3548116 B1 | 4/2022 |
| TW | 200618832 A | 6/2006 |
| WO | 2021099415 A1 | 5/2021 |
| WO | 2021/199034 A1 | 10/2021 |
| WO | 2022/029097 A1 | 2/2022 |

* cited by examiner

130

1330

1320

1310

150

1510

1512'

1512

1513'

1513

1511

160

1630

1620

1610

1310

MEDICAL INJECTION SYSTEM

FIELD

The present disclosure generally relates to a medical injection system and, more particularly, to a medical injection system generating injection initiation feedback prompts after automatic administration.

BACKGROUND

Medical fluids or drugs may be administered to a patient by an injection system. If frequent injections of the drug are deemed necessary for the patient, then the injection system should be portable and readily operable by the patient to improve convenience. Therefore, a portable medical injection system has been commercially available for patients who are in need of daily injections.

A patient may use a portable medical injection system to administer a particular medical fluid or drug by themselves. In using a conventional portable medical injection system, the patient is not informed whether an injection has been initiated or completed. Without being informed whether an injection has been initiated or completed, the patient may remove the injection system too early or too late, which may cause an incomplete injection of the drug or may require more handling time to complete the injection, thus causing great inconvenience to the patient.

SUMMARY

In view of the shortcomings in the art, some embodiments of the present disclosure may provide a medical injection system with automatic injection initiation feedback prompts, especially for a medical injection system with an automatic trigger injection mechanism.

Also, some embodiments of the present disclosure may provide a medical injection system with feedback mechanism for injection completion.

In one aspect of the present disclosure, a medical injection system may include: an injection initiation feedback module, including: an actuator, including an impact plate and one or more impact plate groove on the impact plate; and a click collar, which forms a penetrable structure for accommodating the actuator, and the penetrable structure of the click collar further includes: a click surface, which is configured to corresponding with the impact plate of the actuator; and one or more click surface protrusions configured to resist the click surface from contacting the impact plate, wherein, when the click collar is rotated to accommodate the one or more click surface protrusions in the one or more impact plate grooves, the click surface contacts the impact plate to generate an injection initiation feedback prompt.

According to an implementation of the first aspect, the medical injection system further includes: an injection module, including: a starter having one end which contacts the click collar, wherein the click collar is driven to rotate when the starter rotates, and the starter forms a penetrable structure for accommodating the actuator, wherein the penetrable structure of the starter further includes: an inner annular surface; and one or more accommodating spaces which are arranged on the inner annular surface to protrude outward, wherein the actuator further includes: one or more upper elastic pieces, which are aligned or not with the one or more impact plate grooves, and the inner annular surface presses the one or more upper elastic pieces inward, wherein, when the starter rotates to accommodate the one or more upper elastic pieces of the actuator in the one or more accommodating spaces, the one or more click surface protrusions are simultaneously accommodated in the one or more impact plates grooves of the actuator.

According to another implementation of the first aspect, the click collar further includes one or more rotational protrusions configured to contact the one end of the starter, and the one or more accommodating spaces of the starter are aligned or not with the one or more click surface protrusions of the click collar.

According to another implementation of the first aspect, another end of the starter includes one or more rotational ramps; and the injection module further includes: a needle cover including one or more motion steering protrusions contacting the one or more rotational ramps, and when the needle cover is moved in an axial direction of the medical injection system, the one or more motion steering protrusions push the one or more rotational ramps to cause the starter to rotate around an axis aligned with the axial direction and the click collar is driven to rotate.

According to another implementation of the first aspect, the medical injection system further includes: a cartridge module, including: a plunger including a plunger recess corresponding to the one or more upper elastic pieces, wherein the plunger is configured to be accommodated in the actuator or the needle cover and move in another axial direction of the medical injection system, wherein, the actuator further includes one or more rotating chutes, and when the one or more upper elastic pieces are compressed inward against the plunger recess, the actuator resists the plunger from moving in the other axial direction, and wherein the penetrable structure of the starter further includes: one or more rotational protrusions located on the inner annular surface for rotating the starter by moving along the one or more rotating chutes, wherein the one or more upper elastic pieces are no longer compressed inward by the inner annular surface when the one or more accommodating spaces are rotated to align with the one or more upper elastic pieces.

According to another implementation of the first aspect, the medical injection system may be used with a medicine vial. The vial forms a space for containing a substance to be injected and may include a needle body, and the plunger may be arranged in the space. When the plunger rod moves in the other axial direction of the medical injection system, the plunger may squeeze the substance to be injected from the needle body.

According to another implementation of the first aspect, when the plunger moves in the other axial direction of the medical injection system, the click surface of the click collar contacts the impact plate of the actuator to generate the injection initiation feedback prompt.

According to another implementation of the first aspect, the medical injection system of claim 5, further including a housing for accommodating the cartridge module and the injection module, wherein the actuator is fixed to the housing, and when the cartridge module is pressed down against skin of a subject, the needle cover is moved in the other axial direction of the medical injection system and the one or more motion steering protrusions push the one or more rotational ramps to cause the starter to rotate around an axis aligned with the axial direction.

According to another implementation of the first aspect, the rotating chutes of the actuator are chutes arranged clockwise in the other axial direction.

According to another implementation of the first aspect, the medical injection system further including an injection completion feedback module, wherein the injection completion feedback module includes: a click ring which forms a penetrable structure for accommodating the actuator; and a compression collar which forms a penetrable structure for accommodating the plunger, and an impact surface formed in the penetrable structure of the compression collar corresponding to the click ring, wherein when the click ring contacts the impact surface of the compression collar, an injection completion feedback prompt is generated.

According to another implementation of the first aspect, the actuator further includes one or more lower elastic pieces, and when the one or more lower elastic pieces are pushed outward by the plunger, the one or more lower elastic pieces compress against the click ring to resist the click ring from contacting the impact surface of the compression collar.

According to another implementation of the first aspect, after the plunger moves in the other axial direction of the medical injection system, the plunger no longer pushes the one or more lower elastic pieces of the actuator outward.

According to another implementation of the first aspect, the medical injection system may further include a housing to accommodate the cartridge module and the injection module, and the compression collar is fixed on the housing.

According to another implementation of the first aspect, the impact surface of the compression collar further includes one or more penetrable holes through which the one or more motion steering protrusions of the needle cover pass to contact the rotational protrusions of the starter.

According to another implementation of the first aspect, the compression collar further includes a compression structure to fix the vial.

According to another implementation of the first aspect, the medical injection system further includes a cap structure, wherein the cap structure includes: a cap cover which forms a structure accommodating at least a portion of the cartridge module; and a shield remover which is arranged to be coupled to the cap cover and includes a needle guard remover, wherein when the shield remover is removed from the medical injection system, the needle guard removers removes a needle guard to expose a needle body.

According to another implementation of the first aspect, the shield remover is arranged to accommodate the needle body of the vial, and when the cap structure is detached from the medical injection system, the needle guard remover removes a needle guard corresponding to the needle body to expose the needle body.

According to another implementation of the first aspect, the medical injection system further including a backstop module, wherein the backstop module includes: a front housing which forms a structure accommodating at least a portion of the cartridge module and the injection module and includes one or more fixing holes; and a syringe holder, which is accommodated in the front housing and includes one or more fixing protrusions corresponding to the one or more fixing holes of the front housing to fix the syringe holder to the front housing, and the syringe holder further includes one or more elastic pieces coupled to the needle cover to limit movement of the needle cover in the other axial direction of the medical injection system, wherein the syringe holder further includes one or more fixing pieces relative to the one or more elastic pieces, and when the needle cover moves in the axial direction of the medical injection system, the one or more elastic pieces are compressed to be accommodated in the one or more fixing pieces, and the movement of the needle cover is no longer limited.

According to another implementation of the first aspect, the needle cover further includes one or more buckles, and the front housing further includes one or more annular protrusions, and when the elastic piece no longer limits movement of the needle cover, the needle cover moves in the other axial direction of the medical injection system so that the one or more annular protrusions contact the one or more buckles to limit movement of the needle cover in the axial direction of the medical injection system.

According to another implementation of the first aspect, when the one or more elastic pieces no longer limit movement of the needle cover, the needle cover moves in the other axial direction of the medical injection system, and the one or more fixing protrusions limit a movement range of the needle cover.

In various implementations of the medical injection system of the present disclosure, with the arrangement of the starter, the movement of the needle cover in the axial direction could be used to drive the starter to rotate around the axis aligned with the axial direction, and then to release the restriction of the actuator on the plunger in the cartridge module to trigger the injection. Further, with the arrangement of the actuator combined with the position of the click collar and the starter, the click surface of the click collar and the impact plate of the actuator could contact each other when the injection initiates, and then an injection initiation feedback prompt is generated. Moreover, with the arrangement of the actuator, when the injection is completed, the plunger no longer makes the actuator restrict the click ring to contact the compression collar, and then an injection completion feedback prompt is generated. Therefore, when the user intuitively presses the needle body of the injection system of the present disclosure against the skin, the injection could be automatically triggered, and a prompt would be generated when the injection is completed to improve accuracy and convenience when the user self-administers a medical fluid or drug.

BRIEF DESCRIPTION OF THE DRAWINGS

The present description will be better understood from the following detailed description when read in light of the accompanying drawings, where.

DETAILED DESCRIPTION

Figure 1:
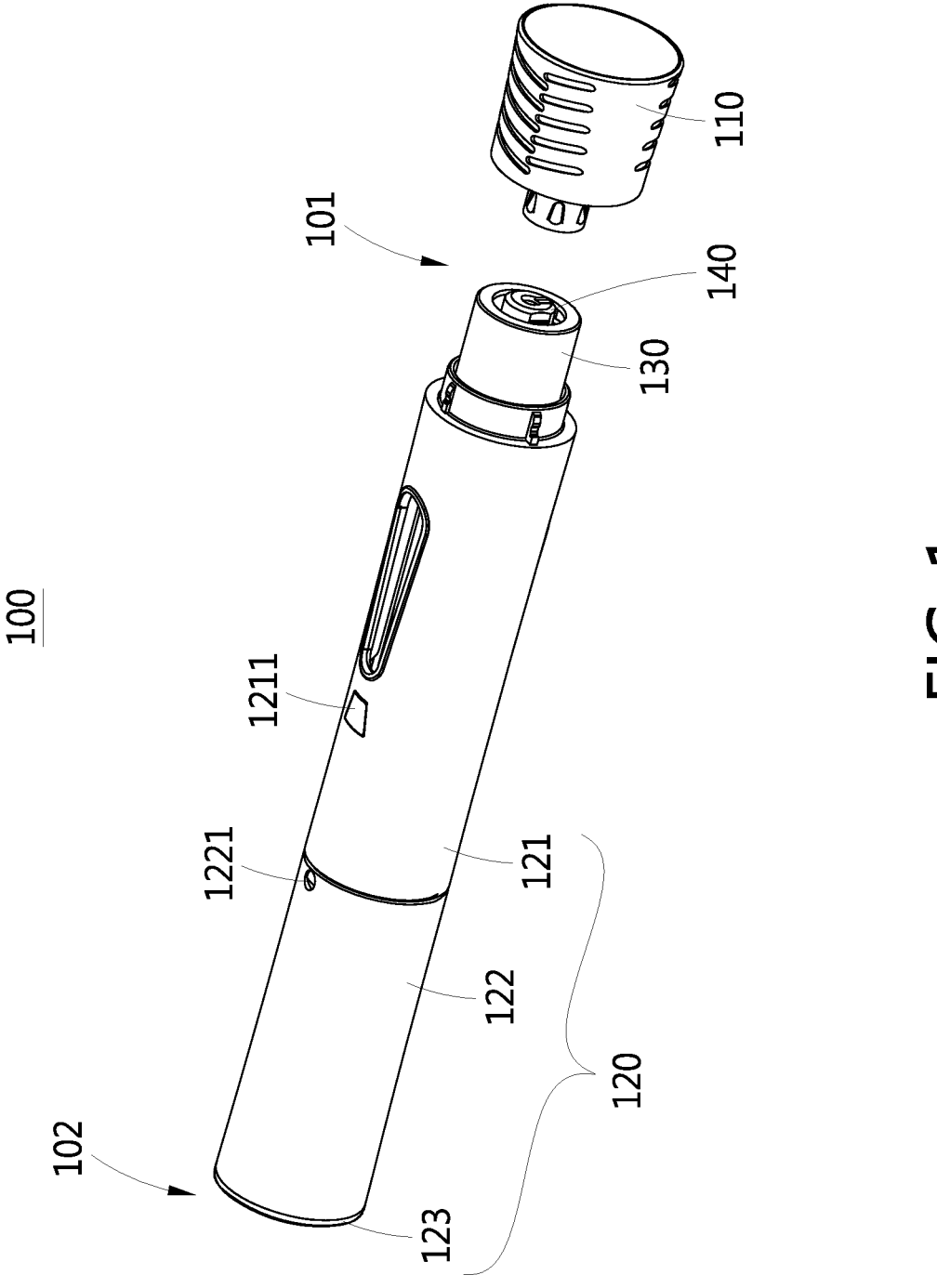
FIG. 1 is a perspective view of a medical injection system, in accordance with an embodiment of the present disclosure.

The following disclosure contains specific information pertaining to exemplary embodiments in the present disclosure. The drawings in the present disclosure and their accompanying detailed disclosure are directed to merely exemplary embodiments. However, the present disclosure is not limited to merely these exemplary embodiments. Other variations and embodiments of the present disclosure will occur to those skilled in the art. Unless noted otherwise, like or corresponding elements among the figures may be indicated by like or corresponding reference numerals. Moreover, the drawings and illustrations in the present disclosure are generally not to scale and are not intended to correspond to actual relative dimensions.

For the purposes of consistency and ease of understanding, like features are identified (although, in some examples, not shown) by numerals in the exemplary figures. However, the features in different embodiments may be different in other respects, and thus shall not be narrowly confined to what is shown in the figures.

Terms such as "at least one embodiment", "one embodiment", "multiple embodiments", "different embodiments", "some embodiments," "present embodiment", and the like may indicate that an embodiment of the present disclosure so described may include a particular feature, structure, or characteristic, but not every possible embodiment of the present disclosure must include a particular feature, structure, or characteristic. Furthermore, repeated use of the phrases "in one embodiment", "in this embodiment", and so on does not necessarily refer to the same embodiment, although they may be identical. Furthermore, the use of phrases such as "embodiments" in connection with "the present disclosure" does not imply that all embodiments of the present disclosure necessarily include a particular feature, structure, or characteristic, and should be understood as "at least some embodiments of the present disclosure" include the particular feature, structure, or characteristic described. The term "coupled" is defined as connected, directly or indirectly through intervening components, and is not necessarily limited to physical connections. The term "comprising" refers to "including but not necessarily limited to", which specifically indicates open-ended inclusion or membership in the so-described combination, group, series, and the equivalent.

Additionally, for the purposes of explanation and non-limitation, specific details such as functional entities, techniques, protocols, standards, and the like are set forth for providing an understanding of the described technology. In other examples, detailed disclosure of well-known methods, technologies, systems, architectures, and the like are omitted so as not to obscure the disclosure with unnecessary details.

The terms "first", "second", and "third" in the description of the present disclosure and the above-mentioned drawings are used to distinguish different objects, rather than to describe a specific order. Furthermore, the term "comprising" and any variations thereof are intended to accommodate non-exclusive inclusions. For example, a process, method, system, product, or device that includes a series of steps or modules is not limited to the listed steps or modules, but optionally also includes steps or modules that are not listed, or optionally also includes other steps or modules that are inherent to those processes, methods, products, or devices.

The term "penetrable structure" in the description of the present disclosure and the above-mentioned drawings refers to a hollow structure that is penetrable at both ends along an axis of the medical injection system. For example, the penetrable structure may be a hollow structure that is penetrable at both ends along the center or not the center of the axis of the medical injection system. Furthermore, the term "hollow structure" refers to a structure hollowed out inside. For example, the hollow structure may be a hollowed structure having a similar shape or a dissimilar shape with respect to the outer shape of the element.

The term "accommodate" in the description of the present disclosure and the above-mentioned drawings means to cover with a specific structure or space to accommodate other elements, and unless otherwise specified, "accommodate" may include "completely accommodate" and/or "partially accommodate".

The present disclosure will be described in further detail below in conjunction with the accompanying drawings and embodiments.

The present disclosure is generally related to a medical injection system that includes a modular design and a cartridge structure. The medical injection system may be used by a user to create a puncture in the skin of a human or mammal (e.g., the same user or another patient) and administer a drug or a medical fluid. In some embodiments, the user may be an individual using the medical injection system of the present disclosure. In some embodiments, the patient may be the same individual as the user or another individual who can be a subject of a drug administration performed by the medical injection system of the present disclosure. Since the medical injection system of the present disclosure can be operated by the same individual (e.g., the patient), the patient and the user described herein may be the same individual. In some embodiments, the drug or the medical fluid may be administered by the medical injection system. In some embodiments, a longitudinal axis may be defined as an axis connecting two ends (e.g., a proximal end and a distal end) of the medical injection system. Moreover, in some embodiments, an axial direction may be defined as a direction along the longitudinal axis (e.g., a first axial direction may be toward the distal end of the medical injection system, and a second axial direction may be toward the proximal end of the medical injection system, or vice versa).

Refer to FIG. 1, which is a perspective view of a medical injection system, in accordance with an embodiment of the present disclosure. The medical injection system 100 may include a cap structure 110, a housing 120, an injection module 130, and a cartridge module 140.

In some embodiments, the housing 120 may further include a front housing 121, a rear housing 122, and a fixed buckle 123. The fixed buckle 123 may be disposed at a proximal end 102 of the medical injection system 100. The rear housing 122 may be detachably coupled to the fixed buckle 123 and disposed near the proximal end 102 of the medical injection system 100. The front housing 121 may be detachably coupled to the rear housing 122 and disposed near a distal end 101 of the medical injection system 100. The housing 120 substantially accommodates the injection module 130 and the cartridge module 140 to form an external shape of the medical injection system 100, such as a cylinder.

In some embodiments, the distal end 101 may be one of the two ends of the medical injection system 100 which is directed toward a puncture site of the patient's skin while using the medical injection system 100. The proximal end 102 may be the other of the two ends of the medical injection system 100 which is opposite to the distal end 101 while using the medical injection system 100.

In some embodiments, the front housing 121 may further include a fixing hole 1211 for being coupled to a fixing protrusion 1731 of a syringe holder 1730 (described below) to detachably fix a backstop module 170 (described below). In some embodiments, the rear housing 122 may further include a fixing hole 1221 for being coupled to a fixing structure 1631 of a compression collar 1630 (described below) to detachably fix an injection completion feedback module 160 (described below).

In some embodiments, the cap structure 110 may be disposed at the distal end 101 of the medical injection system 100 and may be detachably coupled to the front housing 121 to completely accommodate the injection module 130 and the cartridge module 140. In some embodiments, when the cap structure 110 accommodates the injection module 130 and the cartridge module 140, the distal end 101 of the medical injection system 100 may be one of the two ends of the cap structure 110. In some embodiments, the cap structure 110 may further include a plurality of cap components integrated together to form the cap structure 110. In some embodiments, at least one of the cap components in the cap structure 110 is detachably coupled to the front housing 121, and at least one of the cap components is detachably coupled to the injection module 130 or the cartridge module 140. In some embodiments, the cap components in the cap structure 110 coupled to the front housing 121, the injection module 130, or the cartridge module 140 may be the same or different cap components.

In some embodiments, the injection module 130 is configured to automatically trigger the injection when the medical injection system 100 is compressed against the skin. In some embodiments, the injection module 130 may further include a plurality of injection components integrated together to form the injection module 130. In some embodiments, at least one of the injection components in the injection module 130 is detachably coupled to other injection components in the injection module 130. In some embodiments, at least one of the injection components in the injection module 130 is detachably coupled to the cap structure 110, the housing 120, or the cartridge module 140. In some embodiments, the injection module 130 may serve as an operating structure which facilitates the automatic injection function of the medical injection system 100 of the present disclosure.

In some embodiments, a portion of the injection components in the injection module 130 may be partially accommodated in the cap structure 110. In some embodiments, one or more of the injection components may be partially or completely accommodated by the cap structure 110, while the other injection components may not be accommodated by the cap structure 110. In some embodiments, a portion of the components of the injection module 130 may be partially accommodated in the housing 120, such as in the front housing 121, the rear housing 122, or the fixed buckle 123, or in all of the front housing 121, the rear housing 122, and the fixed buckle 123. In some embodiments, one or more of the injection components may be partially or completely accommodated by the housing 120, such as by the front housing 121, the rear housing 122, or the fixed buckle 123, or by all of the front housing 121, the rear housing 122, and the fixed buckle 123, while the other injection components may not be accommodated by the housing 120. In other embodiments, each of the injection components may be partially accommodated by the housing 120. In other embodiments, all injection components may be completely accommodated by the housing 120.

In some embodiments, the cartridge module 140 is configured to accommodate the substance to be injected and deliver the substance through the needle body into the patient. In some embodiments, the cartridge module 140 may further include a plurality of cartridge components integrated together to form the cartridge module 140. In some embodiments, at least one of the cartridge components in the cartridge module 140 is detachably coupled to other cartridge components in the cartridge module 140. The cartridge module 140 may contain a drug or medical fluid to be injected. In some embodiments, at least one of the cartridge components in the cartridge module 140 is detachably coupled to the cap structure 110, the housing 120, or the injection module 130. In some embodiments, at least one of the cartridge components in the cartridge module 140 is detachably fixed to the housing 120, such as to the fixed buckle 123.

In some embodiments, a portion of the cartridge components in the cartridge module 140 may be partially accommodated in the cap structure 110. In some embodiments, one or more of the cartridge components may be partially or completely accommodated by the cap structure 110 while the other cartridge components may not be accommodated by the cap structure 110. In some embodiments, a portion of the cartridge components in the cartridge module 140 may be partially accommodated in the injection module 130. In some embodiments, one or more of the cartridge components may be partially or completely accommodated by the injection module 130 while the other cartridge components may not be accommodated by the injection module 130.

Figure 2:
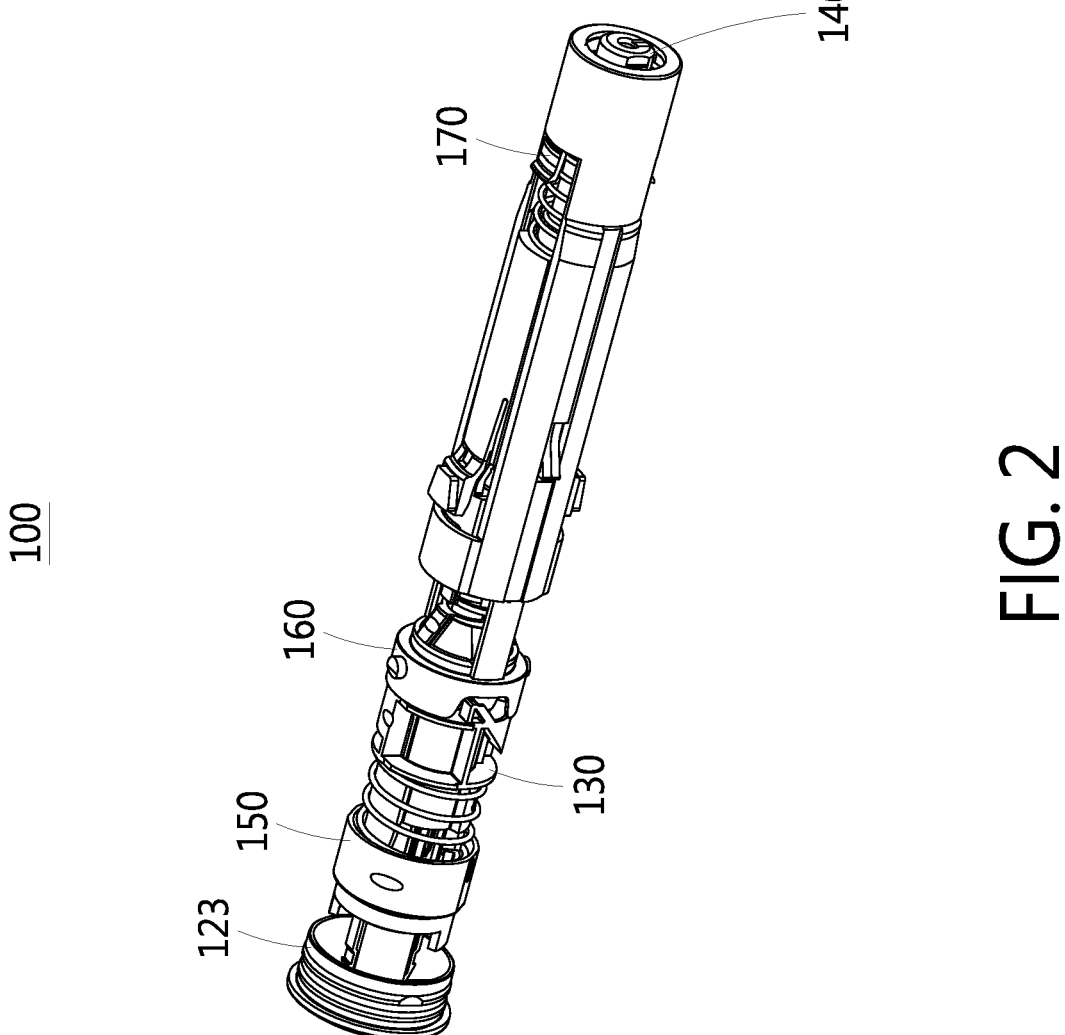
FIG. 2 is a perspective view of the medical injection system, in which a cap structure, a front housing, and a rear housing are removed, in accordance with an embodiment of the present disclosure.

Refer to FIG. 2, which is a perspective view of the medical injection system 100, in accordance with an embodiment of the present disclosure, in which the cap structure 110, the front housing 121, and the rear housing 122 are removed. The medical injection system 100 may further include an injection initiation feedback module 150, an injection completion feedback module 160, and a backstop module 170. Since there are some common components among the injection module 130, the cartridge module 140, the injection initiation feedback module 150, the injection completion feedback module 160, and the backstop module 170, only some components of each module are marked in FIG. 2 to indicate the relative position distribution among the modules, and the components of each module will be explained below in conjunction with the drawings.

In some embodiments, the injection initiation feedback module 150 is configured to generate an injection initiation feedback prompt. In some embodiments, the injection initiation feedback module 150 may be disposed near the proximal end 102 of the medical injection system 100 and may be detachably coupled to one or more of the injection components in the injection module 130. In some embodiments, the injection initiation feedback module 150 may further include a plurality of injection initiation feedback components integrated together to form the injection initiation feedback module 150. In some embodiments, at least one of the injection initiation feedback components in the injection initiation feedback module 150 is detachably coupled to other injection initiation feedback components in the injection initiation feedback module 150. In some embodiments, at least one of the injection initiation feedback components in the injection initiation feedback module 150 is detachably coupled to the injection components in the injection module 130.

In some embodiments, a portion of the injection initiation feedback components in the injection initiation feedback module 150 may partially accommodate one or more of the injection components in the injection module 130. In some embodiments, one or more of the injection initiation feedback components may partially or completely accommodate one or more injection components, while the other injection components may not be accommodated. In other embodiments, the injection initiation feedback module 150 may partially accommodate each of the injection components. In other embodiments, the injection initiation feedback module 150 may completely accommodate all the injection components.

In some embodiments, the injection completion feedback module 160 is configured to generate an injection completion feedback prompt. In some embodiments, the injection completion feedback module 160 may be disposed at the distal end 101 of the medical injection system 100 relative to the injection initiation feedback module 150 and may be detachably coupled to the housing 120 (e.g., the rear housing 122), one or more of the injection components in the injection module 130, and one or more of the cartridge components in the cartridge module 140. In some embodiments, the injection completion feedback module 160 may further include a plurality of injection completion feedback components integrated together to form the injection completion feedback module 160. In some embodiments, at least one of the injection completion feedback components in the injection completion feedback module 160 is detachably coupled to other injection completion feedback components in the injection completion feedback module 160. In some embodiments, at least one of the injection completion feedback components in the injection completion feedback module 160 is detachably coupled to the housing 120, the injection components in the injection module 130, and the cartridge components in the cartridge module 140. In some embodiments, at least one of the injection completion feedback components in the injection completion feedback module 160 is detachably fixed to the front housing 121 or the rear housing 122.

In some embodiments, a portion of the injection completion feedback components in the injection completion feedback module 160 may partially accommodate one or more of the injection components in the injection module 130. In some embodiments, one or more of the injection completion feedback components may partially or completely accommodate one or more of the injection components, while the other injection components may not be accommodated. In other embodiments, the injection completion feedback module 160 may partially accommodate each of the injection components. In other embodiments, the injection completion feedback module 160 may completely accommodate all the injection components.

In some embodiments, the backstop module 170 may be disposed near the distal end 101 of the medical injection system 100 and may be detachably coupled to the housing 120 (e.g., the front housing 121), and one or more of the injection components in the injection module 130. In some embodiments, the backstop module 170 may further include a plurality of backstop components integrated together to form the backstop module 170. In some embodiments, at least one of the backstop components in the backstop module 170 is detachably coupled to other backstop components in the backstop module 170. In some embodiments, at least one of the backstop components in the backstop module 170 is detachably coupled to the housing 120 and the injection components in the injection module 130. In some embodiments, at least one of the backstop components in the backstop module 170 is detachably fixed to the front housing 121 or the rear housing 122.

In some embodiments, the backstop module 170 is configured to prevent the needle body from being exposed again after the injection is completed. In some embodiments, a portion of the backstop components in the backstop module 170 may be partially accommodated in one or more of the injection components in the injection module 130. In some embodiments, one or more of the backstop components may be partially or completely accommodated by one or more of the injection components, while the other backstop components may not be accommodated. In some embodiments, a portion of the components in the backstop module 170 may partially accommodate one or more of the cartridge components in the cartridge module 140. In some embodiments, one or more of the backstop components may partially or completely accommodate one or more of the cartridge components, while the other cartridge components may not be accommodated.

Figure 3:
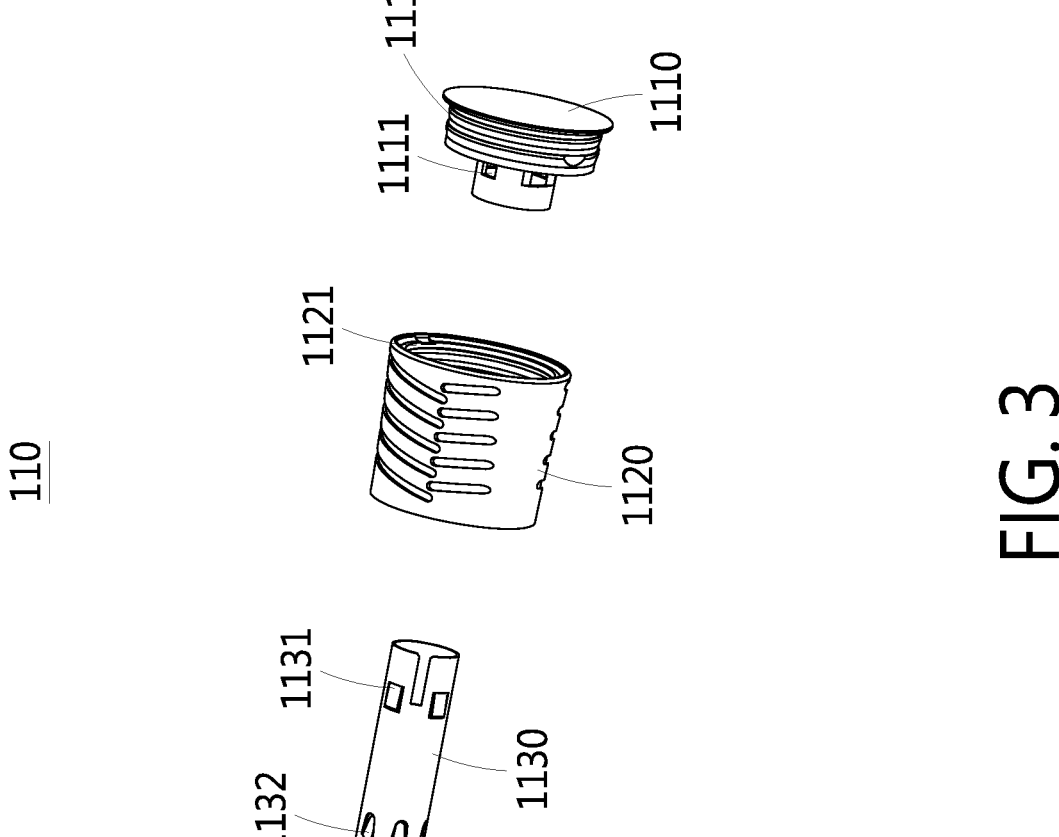
FIG. 3 is an exploded view of the cap structure of the medical injection system, in accordance with an embodiment of the present disclosure.

Refer to FIG. 3, which is an exploded view of the cap structure 110 of the medical injection system 100, in accordance with an embodiment of the present disclosure. The cap components of the cap structure 110 may include a cap cover 1110, a cap body 1120, and a shield remover 1130.

In some embodiments, the cap cover 1110 and the cap body 1120 may substantially form the external shape of the cap structure 110. In some embodiments, the cap cover 1110 may be detachably coupled to at least one of the cap body 1120 and the shield remover 1130. In some embodiments, the cap cover 1110 may include a cap cover fixing structure including one or more cap cover fixing holes 1111, and the shield remover 1130 may include one or more shield remover fixing buckles 1131 to detachably couple the cap cover 1110 and the shield remover 1130. In some embodiments, the cap cover 1110 may include external cap threads 1112 and the cap body 1120 may include internal cap threads 1121 to detachably couple the cap cover 1110 and the cap body 1120.

In some embodiments, the cap body 1120 may be detachably coupled to the front housing 121. In some embodiments, the shield remover 1130 may be detachably coupled to the cartridge module 140. The shield remover 1130 may include one or more needle guard removers 1132, which may be inwardly protruding or claw-like structures for fastening a needle guard 1460 and a case 1470 (described below) in the cartridge module 140, allowing the needle guard 1460 and the case 1470 to be removed along with the cap structure 110 to expose a needle body (e.g., a hollow needle). In the embodiments, the needle guard removers 1132 is claw-like structures.

Figure 4:
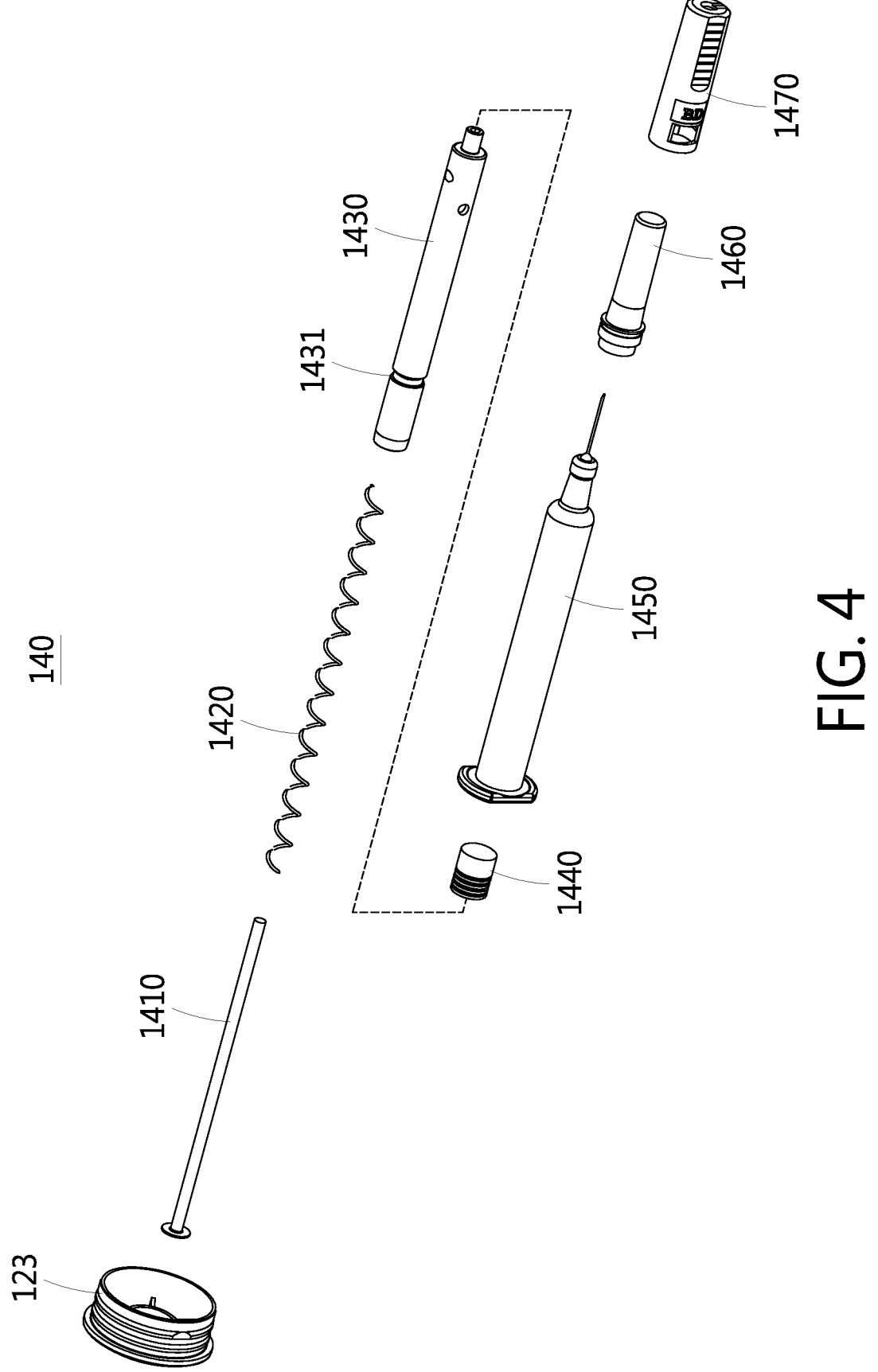
FIG. 4 is an exploded view of a cartridge module of the medical injection system, in accordance with an embodiment of the present disclosure.

Refer to FIG. 4, which is an exploded view of the cartridge module 140 of the medical injection system 100, in accordance with an embodiment of the present disclosure. The cartridge module 140 may include a guide rod 1410, a plunger spring 1420, a plunger 1430, a piston 1440, a vial 1450, a needle guard 1460, and a case 1470, wherein the drug or medical fluid may be contained in the vial 1450. In some embodiments, a hollow needle may be coupled to the vial 1450 for puncturing the patient's skin and administering the drug or medical fluid contained in the cartridge module 140.

Figure 5:
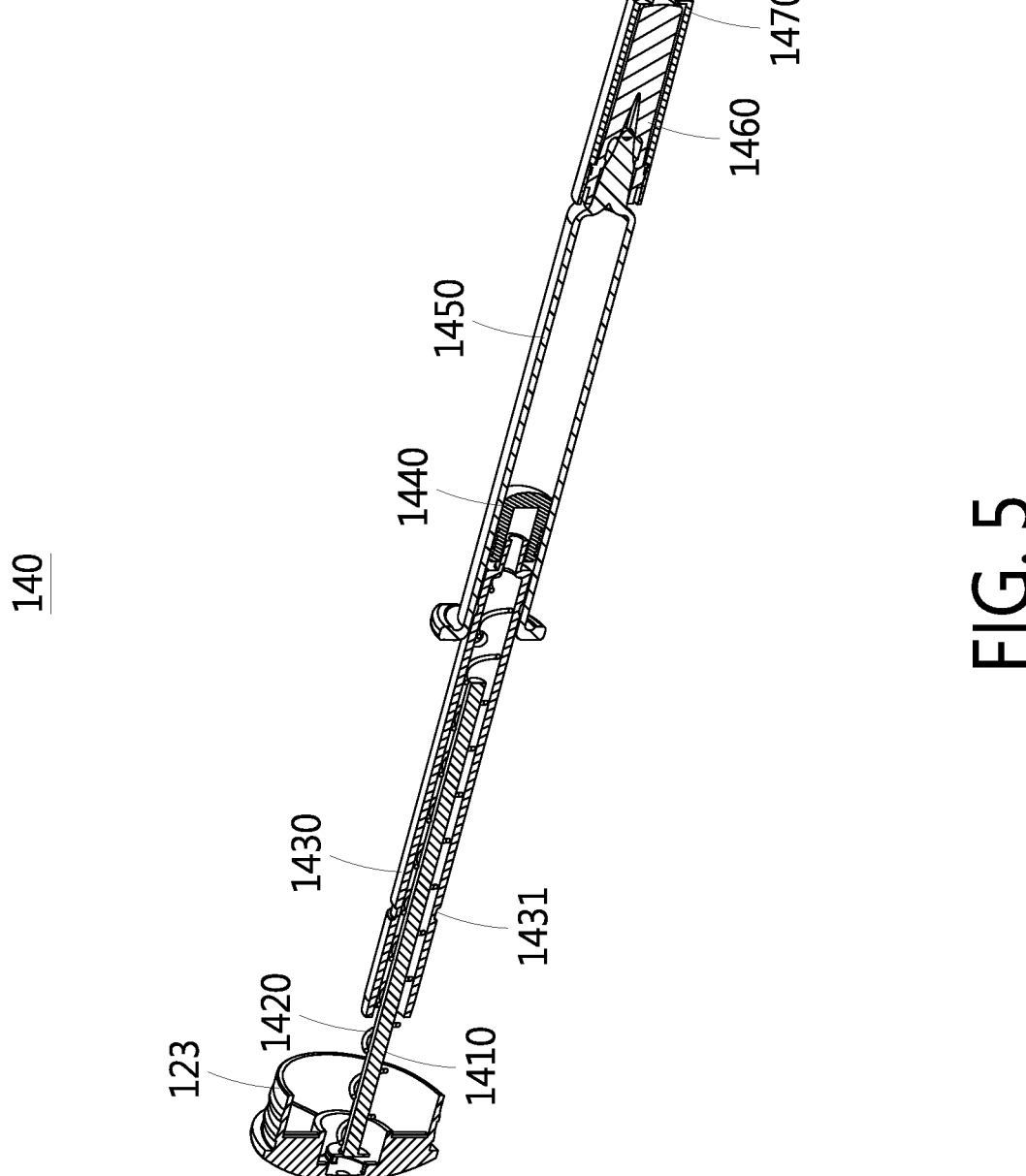
FIG. 5 is a cross-sectional view of the cartridge module of the medical injection system, in accordance with an embodiment of the present disclosure.

Further refer to FIG. 5, which is a cross-sectional view of the cartridge module 140 of the medical injection system 100, in accordance with an embodiment of the present disclosure. In some embodiments, the guide rod 1410 may be detachably fixed to the fixed buckle 123. In some embodiments, the guide rod 1410 may be partially accommodated in the plunger 1430. In some embodiments, the guide rod 1410 may be arranged to pass through the plunger spring 1420 to be accommodated in the plunger 1430. In some embodiments, one of the two ends of the plunger spring 1420 may be detachably fixed to the fixed buckle 123 or the guide rod 1410. In some embodiments, the plunger spring 1420 may be completely accommodated in the plunger 1430, or the other of the two ends may be partially accommodated in the plunger 1430, to drive the plunger 1430 to move toward the distal end 101 of the medical injection system 100.

In some embodiments, the piston 1440 may be disposed in the vial 1450 and coupled to the plunger 1430 to squeeze the drug or medical fluid in the vial 1450 when being pushed by the plunger 1430. In some embodiments, the vial 1450 may be detachably fixed to the compression collar 1630 (described below) in the injection completion feedback module 160 so that the user can arbitrarily replace vials of different specifications. In some embodiments, the needle guard 1460 may detachably accommodate the needle body of the vial 1450. In some embodiments, the case 1470 may detachably accommodate the needle guard 1460. In some embodiments, the needle guard 1460 and the case 1470 may be fastened by the needle guard remover 1132 of the shield remover 1130 so that the needle guard 1460 and the case 1470 may be removed together to expose the needle body when the cap structure 110 is removed from the front housing 121.

In some embodiments, the plunger 1430 may further include a plunger recess 1431 which may be compressed by upper elastic pieces 1312 of an actuator 1310 (described below) in the injection module 130 to restrict the movement of the plunger 1430. When said restriction is lifted, the plunger 1430 may be driven by the plunger spring 1420 to move toward the distal end 101 of the medical injection system 100 to push the piston 1440 so that the volume of the drug or medical fluid in the vial 1450 is reduced, further allowing the drug or medical fluid stored in the vial 1450 to be squeezed out through the needle body.

Figure 6:
FIG. 6 is an exploded view of an injection module of the medical injection system, in accordance with an embodiment of the present disclosure.

Refer to FIG. 6, which is an exploded view of an injection module 130 of the medical injection system 100, in accordance with an embodiment of the present disclosure. The injection module 130 may include an actuator 1310, a starter 1320, and a needle cover 1330.

In further reference to FIG. 1 and FIG. 2, in some embodiments, the actuator 1310 may be disposed at the proximal end 102 of the medical injection system 100, the needle cover 1330 may be disposed at the distal end 101 of medical injection system 100, and the starter 1320 may be disposed between the actuator 1310 and the needle cover 1330. In some embodiments, the actuator 1310, the starter 1320, and the needle cover 1330 may have a penetrable structure individually so that other components of the medical injection system 100 may be accommodated or passed therethrough. In some embodiments, the starter 1320 and the needle cover 1330 may have a penetrable structure individually, while the actuator 1310 may have a hollow structure for accommodating other components (such as the guide rod 1410, the plunger spring 1420, and the plunger 1430).

In some embodiments, the actuator 1310 is configured to limit the movement of the click ring 1620 to control the generation of the injection completion feedback prompt. In some embodiments, the actuator 1310 may be detachably fixed to the fixed buckle 123 and detachably fixed to the compression collar 1630 (described below) in the injection completion feedback module 160. In some embodiments, the actuator 1310 may partially or completely accommodate one or more of the guide rod 1410, the plunger spring 1420, and the plunger 1430 in the cartridge module 140. In some embodiments, the actuator 1310 is configured to limit the movement of the plunger 1430 to control the triggering of the injection. In some embodiments, the actuator 1310 may partially accommodate each of the guide rod 1410, the plunger spring 1420, and the plunger 1430 in the cartridge module 140. In some embodiments, the plunger 1430 may be arranged to pass through the penetrable structure or the hollow structure of the actuator 1310 partially or completely. In some embodiments, the actuator 1310 may be arranged to be partially or completely accommodated in the starter 1320. In some embodiments, the actuator 1310 is configured to generate the injection completion feedback prompt. In some embodiments, the actuator 1310 may be disposed to pass through the penetrable structure of the starter 1320 partially or completely.

In some embodiments, the starter 1320 is configured to control the actuator 1310 to limit the movement of the plunger 1430. In some embodiments, the actuator 1310 may be arranged to pass through the penetrable structure of the starter 1320 partially or completely, allowing the starter 1320 to move flexibly along the longitudinal axis along the actuator 1310. In some embodiments, referring to FIG. 2, the starter 1320 may contact one or more of the needle cover 1330, a click collar 1510 (described below) of the injection initiation feedback module 150, and the compression collar 1630 of the injection completion feedback module 160. In some embodiments, the starter 1320 may contact all of the needle cover 1330, the click ring 151 of the injection initiation feedback module 150, and the compression collar 1630 of the injection completion feedback module 160. In some embodiments, the starter 1320 may contact both the needle cover 1330 and the click ring 151 of the injection initiation feedback module 150.

In some embodiments, the needle cover 1330 is configured to drive the starter to rotate around the axis aligned with the axial direction by the movement in the axial direction. In some embodiments, the needle cover 1330 may partially or completely accommodate one or more of the plunger 1430, the vial 1450, the needle guard 1460, and the case 1470 in the cartridge module 140. In some embodiments, the needle cover 1330 may partially or completely accommodate the compression collar 1630 of the injection completion feedback module 160. In some embodiments, the needle cover 1330 may partially or completely accommodate one or more of a cushion 1710, a connection holder 1720, a syringe holder 1730, and a safety spring 1740 (described below) in the backstop module 170. In some embodiments, the needle cover 1330 is configured to prevent the needle body from being exposed again after the injection is completed. In some embodiments, the components accommodated therein may be arranged to pass through the penetrable structure of the needle cover 1330 partially or completely, allowing the needle cover 1330 to move flexibly along the longitudinal axis.

Figure 7:
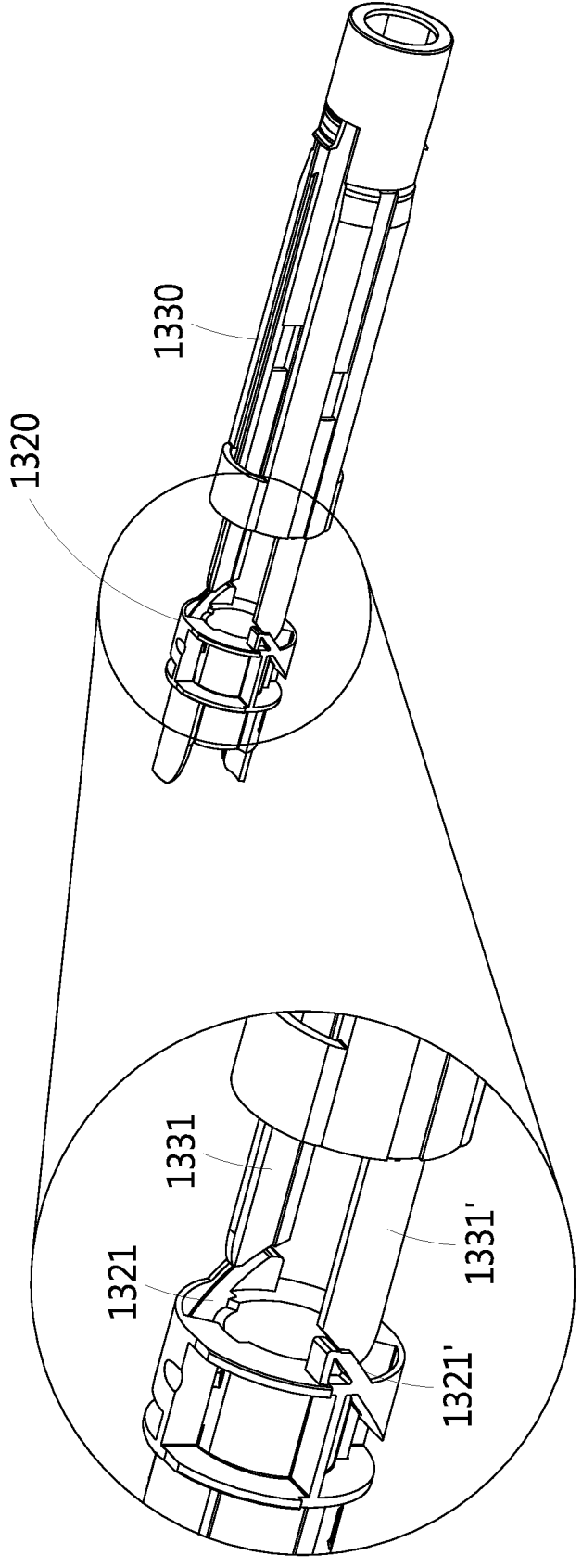
FIG. 7 is a perspective view of an assembly of a starter and a needle cover, in accordance with an embodiment of the present disclosure.

Refer to FIG. 7, which is a perspective view of an assembly of the starter 1320 and the needle cover 1330, in accordance with an embodiment of the present disclosure. In some embodiments, the starter 1320 may include one or more rotational ramps 1321 and 1321', and the rotational ramps 1321 and 1321' may be positioned near the distal end 101 of the medical injection system 100. In some embodiments, the rotational ramps 1321 and 1321' may be arranged in a counterclockwise direction from the distal end 101 toward the proximal end 102. In some embodiments, the needle cover 1330 may further include one or more motion steering protrusions 1331 and 1331', and the motion steering protrusions 1331 and 1331' may contact the rotational ramps 1321 and 1321' of the starter 1320, so that the movement of the needle cover 1330 in the axial direction could be used to drive the starter 1320 to rotate around the axis aligned with the axial direction.

In further reference to FIG. 1, FIG. 2, and FIG. 7, in some embodiments, when the user holds the housing 120 and presses the cartridge module 140 against the patient's skin, the needle cover 1330 may move in the opposite direction of the patient's skin (e.g., toward the proximal end 102 of the medical injection system 100) along the longitudinal axis and make the motion steering protrusions 1331 and 1331' push the rotational ramps 1321 and 1321' to cause the starter 1320 to rotate around the longitudinal axis.

Figure 8:
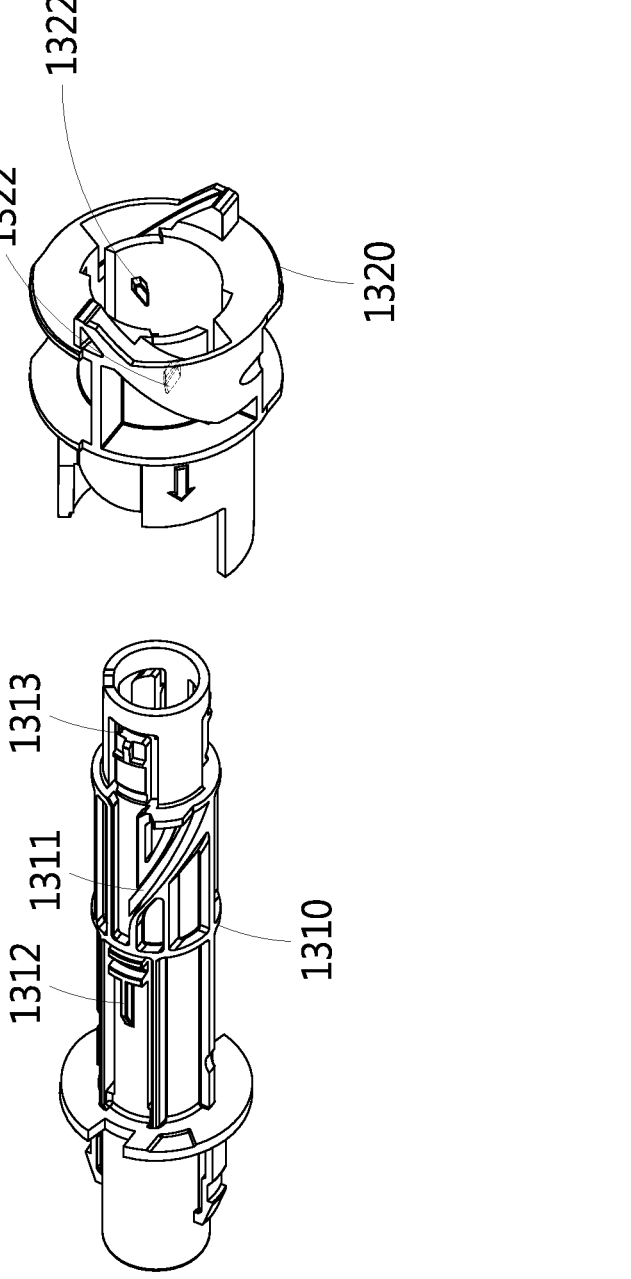
FIG. 8 is a perspective view of an actuator and the starter, in accordance with an embodiment of the present disclosure.

Refer to FIG. 7 and FIG. 8, which is a perspective view of the actuator 1310 and the starter 1320, in accordance with an embodiment of the present disclosure. In some embodiments, the actuator 1310 may further include one or more rotating chutes 1311, one or more upper elastic pieces 1312, and one or more lower elastic pieces 1313. In some embodiments, the actuator 1310 may be arranged from the proximal end 102 to the distal end 101 in the order of the upper elastic piece 1312, the rotating chute 1311, and the lower elastic piece 1313. In some embodiments, the rotating chute 1311 may be a groove arranged in a clockwise direction from the distal end 101 toward the proximal end 102. In some embodiments, an inclination angle of the rotating chute 1311 may be the same as an inclination angle of the rotational ramps 1321 and 1321' of the starter 1320, allowing the starter 1320 to rise along the rotational ramps 1321 and 1321' when rotating (e.g., move toward the proximal end 102). In some embodiments, the length of the rotating chute 1311 may be arranged relative to the rising range of the needle cover 1330. For example, when the needle cover 1330 rises by 10~15 millimeters (mm), preferably 10~12 mm, more preferably 10.5~12 mm), the starter 1320 may rotate along the rotating chute 1311 to rise by 6 mm. In some embodiments, the rotating chute 1311 may be a chute arranged in a clockwise direction from the distal end 101 toward the proximal end 102 and may be further connected to another chute arranged along the longitudinal axis.

In some embodiments, the upper elastic pieces 1312 of the actuator 1310 may include one or more inwardly first protruding blocks for compressing the plunger recess 1431 of the plunger 1430. In some embodiments, the lower elastic piece 1313 of the actuator 1310 may include one or more outwardly second protruding blocks for resisting the click ring 1620 (described below). In some embodiments, the upper elastic piece 1312 of the actuator 1310 may be arranged along the inner diameter range of the actuator 1310 when the upper elastic piece 1312 is not subjected to an external force (e.g., not pushed outward by the plunger 1430). In some embodiments, the lower elastic piece 1313 of the actuator 1310 may be arranged along the inner diameter range of the actuator 1310 when the lower elastic piece 1313 is not subjected to an external force (e.g., not pushed outward by the plunger 1430). In some embodiments, the upper elastic piece 1312 of the actuator 1310 may be partially or completely arranged outside the inner diameter of the actuator 1310 when the upper elastic piece 1312 is not subjected to an external force (e.g., not compressed inward by the starter 1320). In some embodiments, the lower elastic piece 1313 of the actuator 1310 may be partially or completely arranged within the inner diameter of the actuator 1310 when the lower elastic piece 1313 is not subjected to an external force (e.g., not pushed outward by the plunger 1430).

In some embodiments, the starter 1320 may further include one or more rotational protrusions 1322 and 1322', and the rotational protrusions 1322 and 1322' may be arranged on a surface of the penetrable structure of the starter 1320. In some embodiments, the actuator 1310 may partially pass through the penetrable structure of the starter 1320. For example, the starter 1320 accommodates the rotating chute 1311 and the upper elastic piece 1312 of the actuator 1310, and when the starter 1320 rotates around the longitudinal axis, the rotational protrusions 1322 and 1322' therein may slide along the rotating chute 1311 of the actuator 1310. In some embodiments, when sliding along the rotating chute 1311 of the actuator 1310 to near the end of the chute, the rotational protrusions 1322 and 1322' of the starter 1320 may be moved toward the other chute arranged along the longitudinal axis by the pressure of the needle cover spring 1520 (described below) of the injection initiation feedback module 150.

In some embodiments, alternatively, the actuator 1310 may include one or more rotational protrusions, and the starter 1320 may further include one or more rotating chutes, and when the starter 1320 rotates around the longitudinal axis, the rotating chute therein may slide along the rotational protrusions of the actuator 1310.

Figure 9:
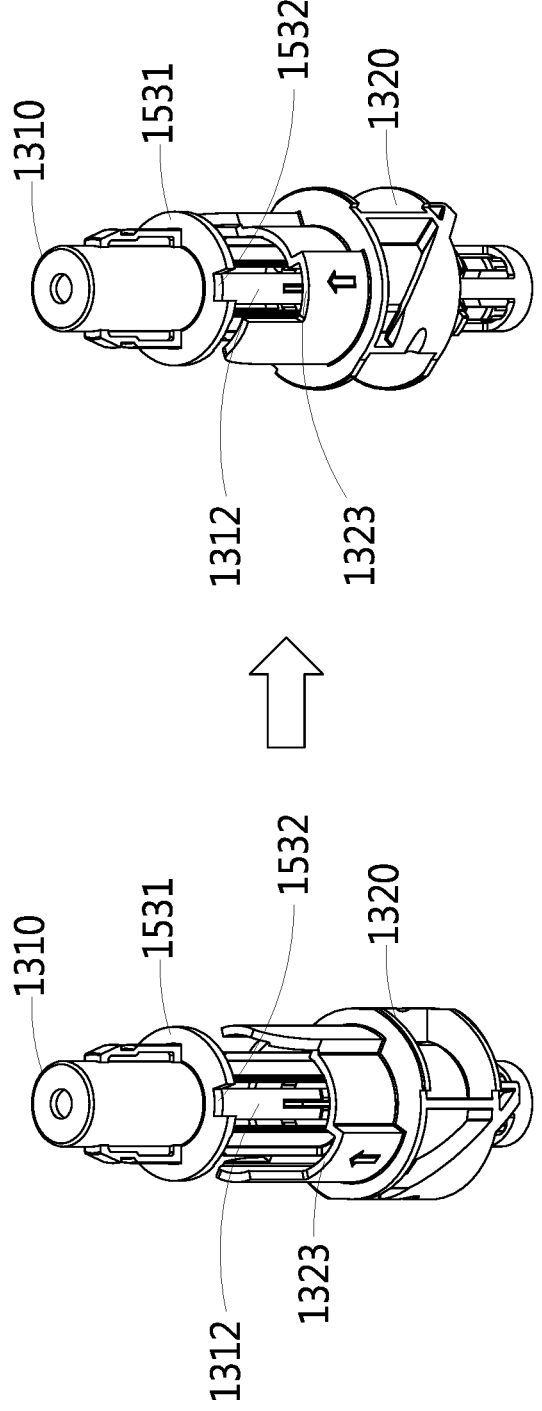
FIG. 9 is a perspective view of an assembly of the actuator and the starter, in accordance with an embodiment of the present disclosure.
Figure 10:
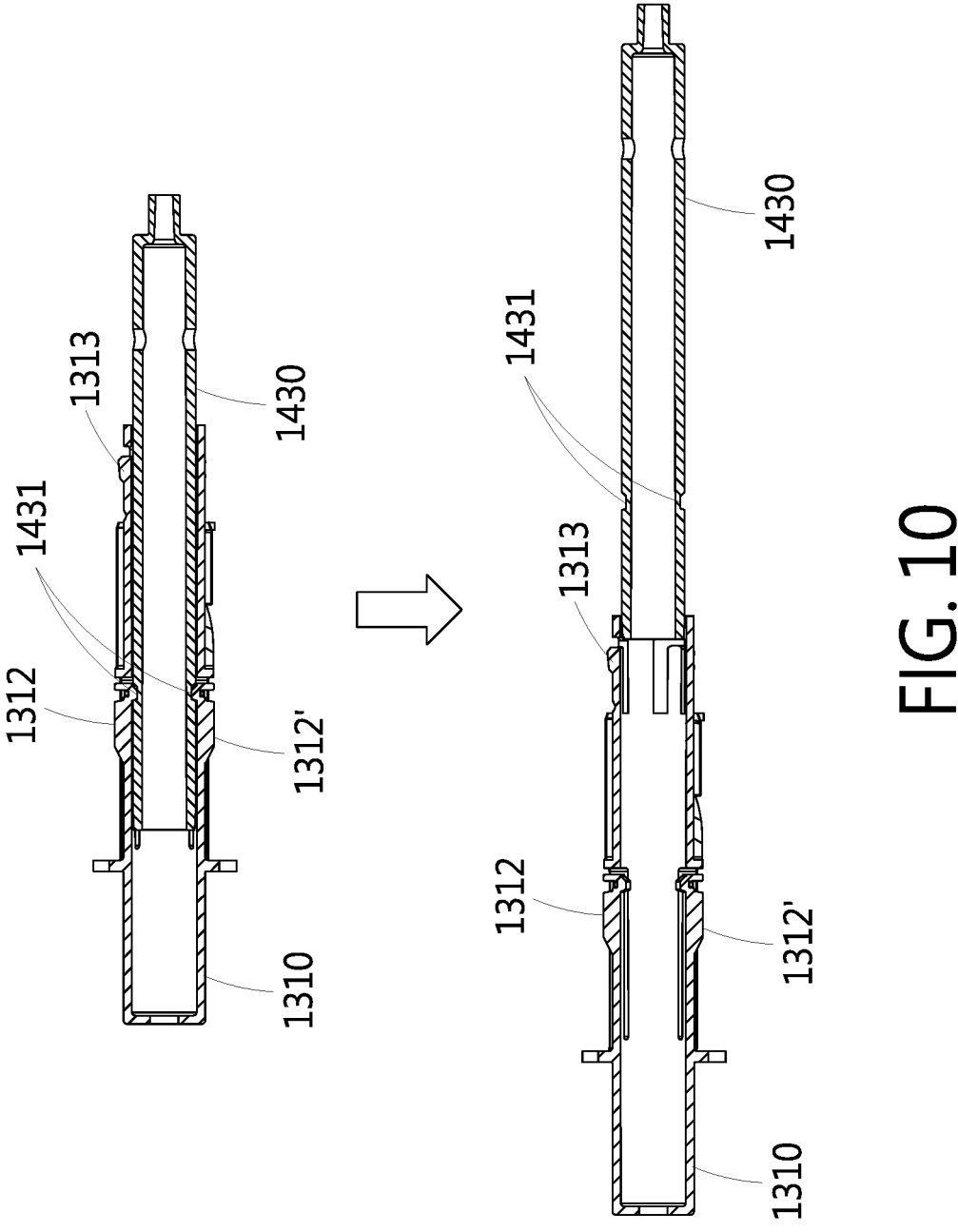
FIG. 10 is a cross-sectional view of an assembly of the actuator and a plunger, in accordance with an embodiment of the present disclosure.

Refer to FIG. 9 and FIG. 10, wherein FIG. 9 is a perspective view of an assembly of the actuator 1310 and the starter 1320, in accordance with an embodiment of the present disclosure, and FIG. 10 is a cross-sectional view of an assembly of the actuator 1310 and the plunger 1430, in accordance with an embodiment of the present disclosure. In some embodiments, the starter 1320 may further include an inner annular surface arranged to compress the upper elastic pieces 1312 inwardly, and may include one or more accommodating spaces 1323 located on the inner annular surface, which may include an accommodating groove protruding outward from the inner annular surface relative to the inner diameter range of the starter 1320, or may include an accommodating gap on the inner annular surface of the starter 1320.

In some embodiments, the upper elastic pieces 1312 of the actuator 1310 are arranged along the inner diameter range of the actuator 1310 when the upper elastic pieces 1312 are not subjected to an external force. When the starter 1320 is not yet pushed by the needle cover 1330 to rotate around the longitudinal axis, the upper elastic pieces 1312 and 1312' of the actuator 1310 may be compressed by the inner annular surface of the starter 1320 so that the driving force of the plunger spring 1420 on the plunger 1430 would not push the elastic pieces 1312 and 1312' outward. Therefore, the upper elastic pieces 1312 and 1312' may compress the plunger recess 1431 of the plunger 1430 to limit the movement of the plunger 1430. After the starter 1320 is pushed by the needle cover 1330 and rotates around the longitudinal axis, the accommodating space 1323 of the starter 1320 may be aligned with the upper elastic pieces 1312 and 1312' of the actuator 1310, allowing the upper elastic pieces 1312 and 1312' to be no longer subjected to the inward force from the inner annular surface. At this time, the driving force of the plunger spring 1420 on the plunger 1430 may release the upper elastic pieces 1312 and 1312' outward, allowing the limit from the upper elastic piece 1312 on the movement of the plunger 1430 to be removed. Therefore, the plunger 1430 may be moved toward the distal end 101 of the medical injection system 100 so that the drug or medical fluid may be squeezed out through the needle body.

In some embodiments, the upper elastic pieces 1312 of the actuator 1310 are arranged outside the inner diameter range of the actuator 1310 when the upper elastic pieces 1312 are not subjected to an external force. When the starter 1320 is not yet pushed by the needle cover 1330 to rotate around the longitudinal axis, the upper elastic pieces 1312 and 1312' of the actuator 1310 may be compressed by the inner annular surface of the starter 1320. Therefore, the upper elastic pieces 1312 and 1312' may compress the plunger recess 1431 of the plunger 1430 to limit the movement of the plunger 1430. After the starter 1320 is pushed by the needle cover 1330 and rotates around the longitudinal axis, the accommodating space 1323 of the starter 1320 may be aligned with the upper elastic pieces 1312 and 1312' of the actuator 1310, allowing the upper elastic pieces 1312 and 1312' to be no longer subjected to the external force from the inner annular surface and then released outward. Therefore, the limit from the upper elastic piece 1312 on the movement of the plunger 1430 is removed. At this time, the plunger 1430 may be driven by the plunger spring 1420 to move toward the distal end 101 of the medical injection system 100 so that the drug or medical fluid may be squeezed out through the needle body.

In some embodiments, when the rotational protrusions 1322 and 1322' rotate along the rotating chute 1311 and rise by 4 mm, the inclination angle of the rotational protrusions 1322 and 1322' may be 45 degrees and the needle cover spring 1520 may drive the starter 1320 toward the other chute arranged along the longitudinal axis. In that case, the starter 1320 rotates to the right and the inclination angle of the rotational protrusions 1322 and 1322' would be 45 degrees, allowing the upper elastic piece 1312 of the actuator 1310 to align with the accommodating space 1323 of the starter 1320.

Therefore, in the medical injection system of the present disclosure, with the arrangement of the starter 1320, the movement of the needle cover 1330 in the axial direction could be used to drive the starter 1320 to rotate around the axis aligned with the axial direction, and then to release the restriction of the actuator 1310 on the plunger 1430 in the cartridge module 140 to trigger the injection.

Figure 11:
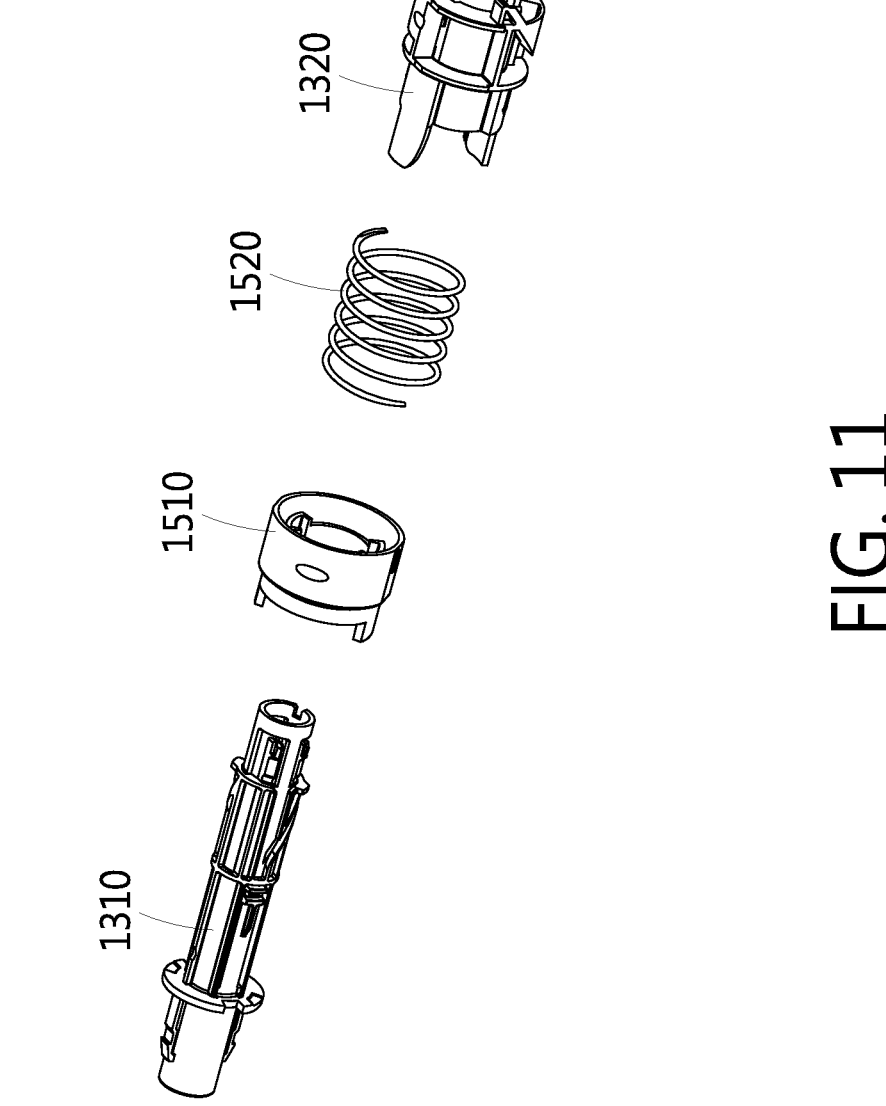
FIG. 11 is an exploded view of an injection initiation feedback module of the medical injection system, in accordance with an embodiment of the present disclosure.

Refer to FIG. 11, which is an exploded view of an injection initiation feedback module 150 of the medical injection system 100, in accordance with an embodiment of the present disclosure. The injection initiation feedback module 150 may include a click collar 1510, the actuator 1310, a needle cover spring 1520, and the starter 1320.

In some embodiments, further referring to FIG. 9, the actuator 1310 may further include an impact plate 1531 and an impact plate groove 1532. In some embodiments, the impact plate 1531 and the impact plate groove 1532 of the actuator 1310 may be disposed near the proximal end 102 of the medical injection system 100 relative to the upper elastic pieces 1312, the rotating chutes 1311, and the lower elastic pieces 1313. In some embodiments, the impact plate groove 1532 of the actuator 1310 may be arranged in alignment with the upper elastic pieces 1312. In some embodiments, the impact plate groove 1532 of the actuator 1310 may not be arranged in alignment with the upper elastic pieces 1312. In some embodiments, further referring to FIG. 2, the click collar 1510 may have a penetrable structure so that other components of the medical injection system 100 may be accommodated or passed therethrough. In some embodiments, the actuator 1310 may partially or completely pass through the penetrable structure of the click collar 1510. In some embodiments, the upper elastic pieces 1312, the rotating chutes 1311, and the lower elastic pieces 1313 of the actuator 1310 may partially or completely pass through the penetrable structure of the click collar 1510. In some embodiments, the click collar 1510 may partially or completely accommodate the needle cover spring 1520 and the starter 1320. In some embodiments, the starter 1320 may be arranged to pass through the needle cover spring 1520 partially or completely, then being partially accommodated within the click collar 1510. In some embodiments, the needle cover spring 1520 may drive the click collar 1510 to move toward the proximal end 102 of the medical injection system 100. In some embodiments, the needle cover spring 1520 may drive the starter 1320 to move toward the distal end 101 of the medical injection system 100.

Figure 12:
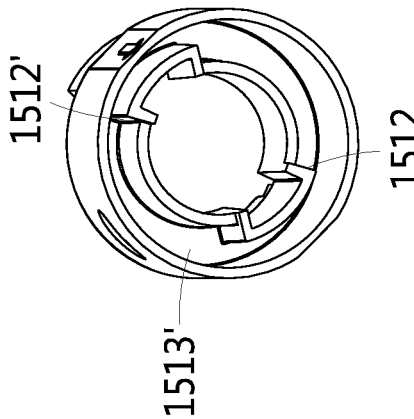
FIG. 12 is a perspective lateral and bottom view of a click collar of the medical injection system, in accordance with an embodiment of the present disclosure.
Figure 12:
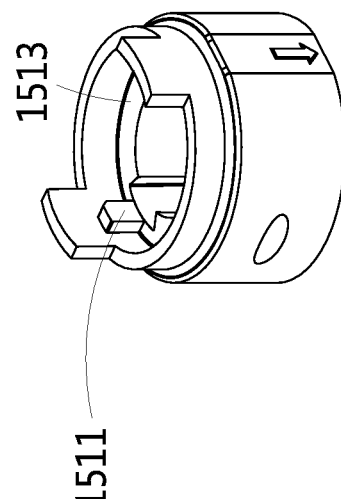

Refer to FIG. 12, which is a perspective lateral and bottom view of the click collar 1510, in accordance with an embodiment of the present disclosure. The click collar 1510 may further form a click surface 1513 corresponding to the impact plate 1531 in the penetrable structure, and may further include click surface protrusions 1511 on the click surface 1513. In some embodiments, one of the click surface protrusions 1511 and the click surface 1513 of the click collar 1510 may contact the impact plate 1531 of the actuator 1310. In some embodiments, the click surface protrusions 1511 of the click collar 1510 may be arranged in alignment with the accommodating space 1323 of the starter 1320 (see, e.g., FIG. 9). In one embodiment, the actuator 1310 may partially or completely pass through the penetrable structure of the click collar 1510, allowing the impact plate 1531 to contact the click surface protrusions 1511 or the click surface 1513. In some embodiments, the backside 1513' of the click surface 1513 of the click collar 1510 may further include rotational protrusions 1512 and 1512'. In some embodiments, the starter 1320 may contact the rotational protrusions 1512 and 1512' of the click collar 1510 so that when rotating around the longitudinal axis, the starter 1320 may concomitantly push the click collar 1510 to rotate around the longitudinal axis. In some embodiments, one end of the two ends of the needle cover spring 1520 may contact or detachably fixed to the backside 1513' of the click surface 1513 of the click collar 1510.

In some embodiments, when the starter 1320 is not yet pushed by the needle cover 1330 to rotate around the longitudinal axis, the click surface protrusions 1511 of the click collar 1510 may contact the impact plate 1531 of the actuator 1310 and resist the click surface 1513 of the click collar 1510 and the impact plate 1531 of the actuator 1310 from contacting. After the starter 1320 is pushed by the needle cover 1330 and rotates around the longitudinal axis, the click collar 1510 may be driven to rotate around the longitudinal axis until the click surface protrusion 1511 of the click collar 1510 is aligned with the impact plate groove 1532 of the actuator 1310 and is accommodated therein. At this time, the needle cover spring 1520 may drive the click collar 1510 to move toward the proximal end 102 of the medical injection system 100 so that the click surface 1513 of the click collar 1510 may contact and collide with the impact plate 1531 of the actuator 1310 to make a sound and generate an impact feeling to alert the user.

In some embodiments, when the accommodating space 1323 of the starter 1320 are aligned with the upper elastic pieces 1312 and 1312' of the actuator 1310 and then trigger the movement of the plunger 1430 (e.g., at the initiation of the injection), the click surface protrusions 1511 of the click collar 1510 may be aligned with the impact plate groove 1532 of the actuator 1310 at the same time to trigger the alert sound and the impact feeling as a feedback mechanism for injection initiation to alert the user that the injection has been triggered to initiate. For example, referring to both FIG. 9 and FIG. 12, when the starter 1320 and the click collar 1510 are rotating in a counterclockwise direction around the longitudinal axis, the impact plate groove 1532 of the actuator 1310 may be arranged at a position aligned with the upper elastic pieces 1312, and the part of the starter 1320 which contacts the rotational protrusions 1512 and 1512' may be arranged at a position relative to the left side of the accommodating space 1323, and the rotational protrusions 1512 and 1512' may be arranged at a position relative to the left side of the click surface protrusions 1511. However, in some embodiments, the impact plate groove 1532 of the actuator 1310 may not be aligned with the upper elastic pieces 1312, as long as the impact plate groove 1532 is arranged so that the click surface protrusions 1511 of the click collar 1510 may be aligned with the impact plate groove 1532 of the actuator 1310 at the same time when the injection starts.

Therefore, with the arrangement of the actuator 1310 and the click collar 1510, together with the arrangement of the starter 1320, the injection initiation feedback prompt is generated when the injection initiates.

Figure 13:
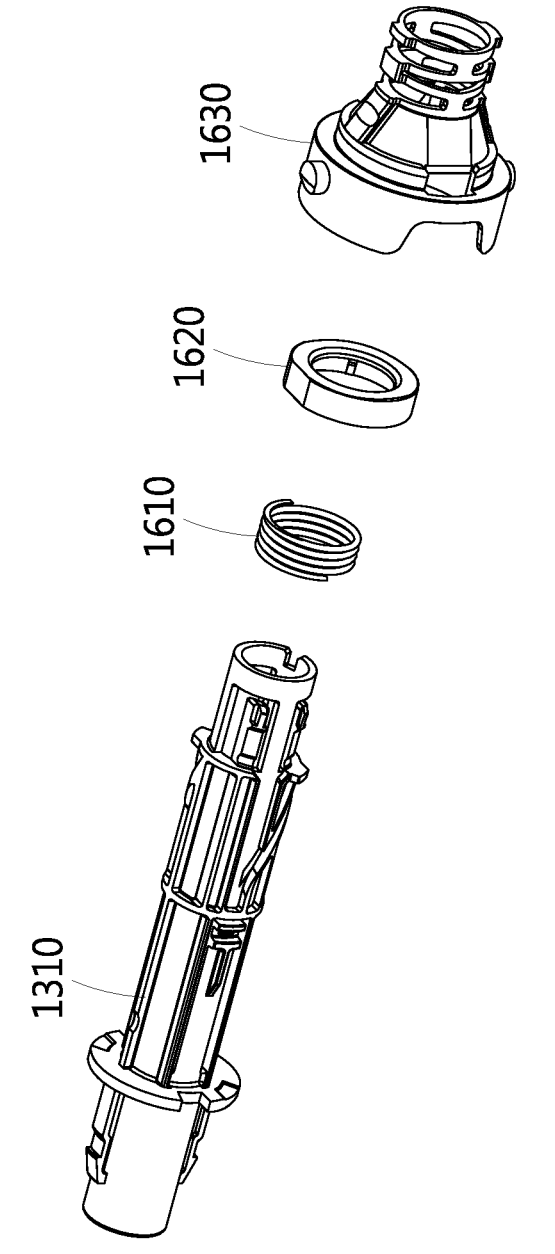
FIG. 13 is an exploded view of an injection completion feedback module of the medical injection system, in accordance with an embodiment of the present disclosure.

Refer to FIG. 13, which is an exploded view of an injection completion feedback module 160 of the medical injection system 100, in accordance with an embodiment of the present disclosure. The injection completion feedback module 160 may include the actuator 1310, a click ring spring 1610, a click ring 1620, and a compression collar 1630.

In some embodiments, the click ring 1620 and the compression collar 1630 may have a penetrable structure individually so that other components of the medical injection system 100 may be accommodated or passed therethrough. In some embodiments, the actuator 1310 may be arranged partially or completely pass through the penetrable structure of the click ring 1620. In some embodiments, the actuator 1310 may be arranged to pass completely through the click ring spring 1610 and partially or completely through the penetrable structure of the click ring 1620. In some embodiments, the click ring spring 1610 may drive the click ring 162 to move toward the distal end 101 of the medical injection system 100. In some embodiments, further referring to FIG. 8, the lower elastic pieces 1313 of the actuator 1310 may completely pass through the penetrable structure of the click ring 1620 to limit the movement of the click ring 1620 when lower elastic pieces 1313 are pushed outward by the plunger 1430. In some embodiments, the penetrable structure of the compression collar 1630 may be at least partially or completely passed through by the plunger 1430.

Figure 14:
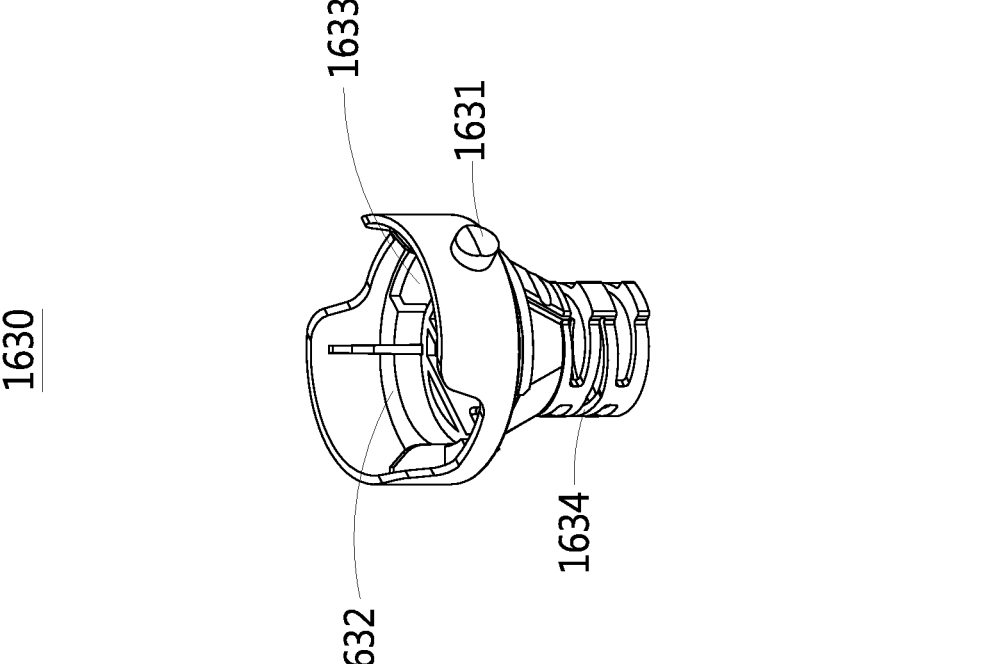
FIG. 14 is a perspective view of a compression collar of the medical injection system, in accordance with an embodiment of the present disclosure.

Refer to FIG. 14 which is a perspective view of the compression collar 1630, in accordance with an embodiment of the present disclosure. The compression collar 1630 may further include a fixing structure 1631, an impact surface 1632, one or more penetrable holes 1633, and a compression structure 1634.

In some embodiments, further referring to FIG. 1 and FIG. 2, the fixing structure 1631 may be coupled to the fixing hole 1221 of the rear housing 122, allowing the compression collar 1630 to be detachably fixed to the housing 120. Compared to conventional uses of springs alone, which require separate fixed springs, the fixing structure 1631 may be more favorable for the manufacture and assembly of medical injection systems. In some embodiments, the impact surface 1632 may be formed relative to the click ring 1620 in the penetrable structure of the compression collar 1630. In some embodiments, the impact surface 1632 may be formed by any flat surface that may be collided with to generate sounds, such as an annular surface extending inwardly of the rear housing 122. In some embodiments, further referring to FIG. 2 and FIG. 7, one or more of the penetrable holes 1633 may be formed on the impact surface 1632, possibly allowing the motion steering protrusions 1331 and 1331' of the needle cover 1330 to pass through and contact the starter 1320. In some embodiments, the compression structure 1634 may detachably fix the vial 1450 to provide a downward resisting force to the vial 1450 when the cartridge module 140 is pressed against the patient's skin. In some embodiments, the compression structure 1634 may be such that tolerances exist at the ends of the vials 1450 to accommodate different specifications of the vials 1450.

In some embodiments, further referring to FIG. 10, the lower elastic piece 1313 of the actuator 1310 shown therein is arranged along the inner diameter range of the actuator 1310 when the lower elastic piece 1313 is not subjected to an external force. Before the plunger 1430 moves toward the distal end 101 of the medical injection system 100 or when the plunger 1430 has not completely moved out of the range of the lower elastic piece 1313 of the actuator 1310, the lower elastic piece 1313 of the actuator 1310 may be pushed outward by the plunger 1430 so that the driving force of the click ring spring 1610 to the click ring 1620 would not compress the lower elastic pieces 1313 inward. Therefore, the lower elastic piece 1313 may limit the movement of the click ring 1620. When the plunger 1430 completely moves out of the range of the lower elastic piece 1313 of the actuator 1310 (e.g., when the injection is completed), the lower elastic piece 1313 of the actuator 1310 may no longer be subjected to the outward force from the plunger 1430. At this time, the driving force of the click ring spring 1610 on the click ring 1620 may compress the lower elastic piece 1313 inward, allowing the limit from the lower elastic piece 1313 on the movement of the click ring 1620 to be removed. Therefore, the click ring 1620 may be moved toward the distal end 101 of the medical injection system 100, and the click ring 1620 may be collided with the impact surface 1632 of the compression collar 1630 to generate a sound and an impact feeling to alert the user that the injection has been completed.

In some embodiments, the lower elastic piece 1313 of the actuator 1310 is arranged inside the inner diameter range of the actuator 1310 when the lower elastic piece 1313 is not subjected to an external force. Before the plunger 1430 moves toward the distal end 101 of the medical injection system 100 or when the plunger 1430 has not completely moved out of the range of the lower elastic piece 1313 of the actuator 1310, the lower elastic piece 1313 of the actuator 1310 may be pushed outward by the plunger 1430 so that the lower elastic piece 1313 may limit the movement of the click ring 1620. When the plunger 1430 completely moves out of the range of the lower elastic piece 1313 of the actuator 1310 (e.g., when the injection is completed), the lower elastic piece 1313 of the actuator 1310 may no longer be subjected to the external force from the plunger 1430 and then released inwardly. Therefore, the limit from the lower elastic piece 1313 on the movement of the click ring 1620 is removed. At this time, the click ring 1620 may be driven by the click ring spring 1610 to move toward the distal end 101 of the medical injection system 100, and then the click ring 1620 may be collided with the impact surface 1632 of the compression collar 1630 to generate a sound and an impact feeling to alert the user that the injection has been completed.

Therefore, with the arrangement of the actuator 1310, when the injection is completed, the plunger 1430 no longer makes the actuator 1310 restrict the click ring 1620 to contact the compression collar 1630, and then an injection completion feedback prompt is generated.

Figure 15:
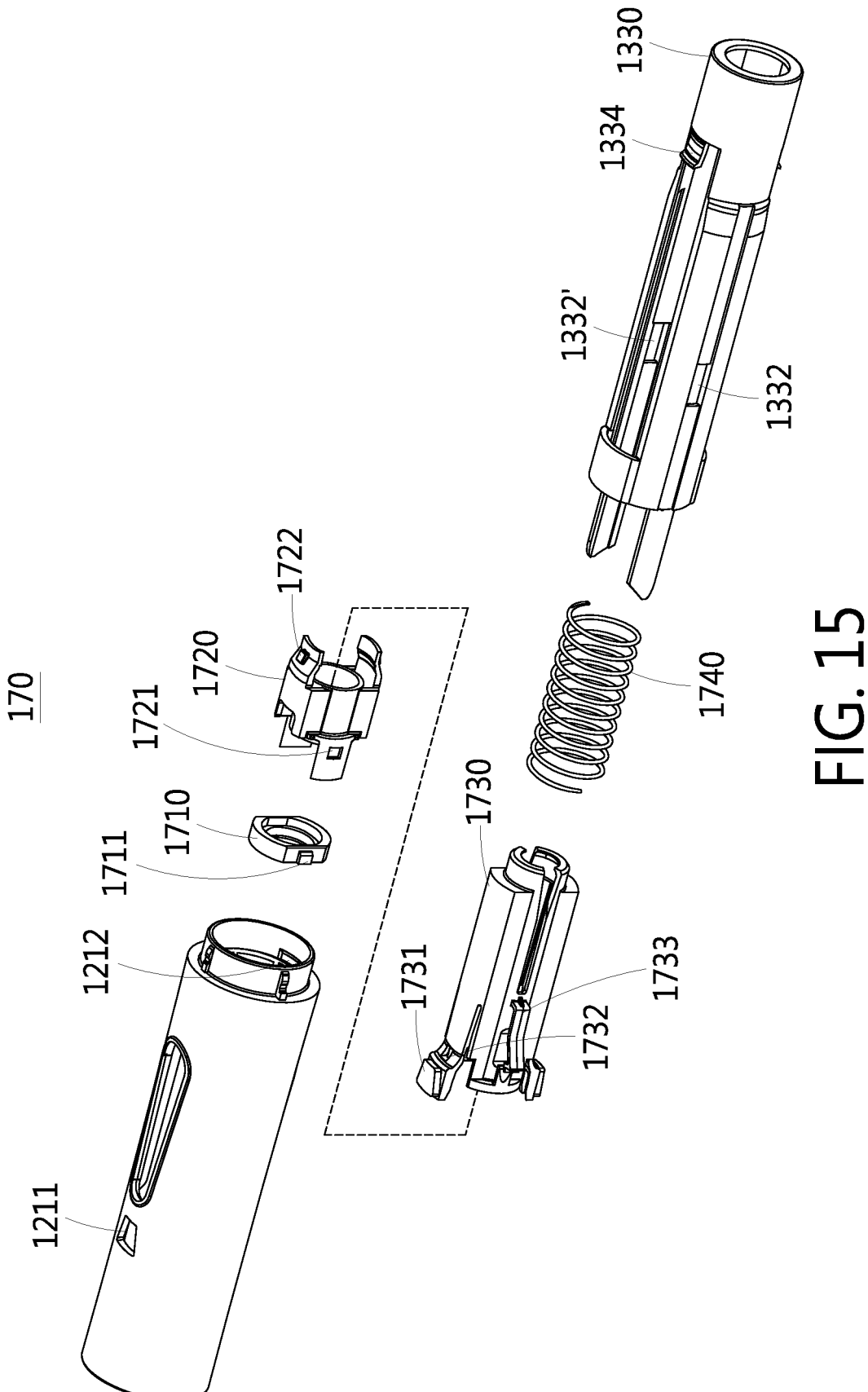
FIG. 15 is an exploded view of a backstop module of the medical injection system, in accordance with an embodiment of the present disclosure.

Refer to FIG. 15, which is an exploded view of the backstop module 170 of the medical injection system 100, in accordance with an embodiment of the present disclosure. The backstop module 170 may include the front housing 121, a cushion 1710, a connection holder 1720, a syringe holder 1730, a safety spring 1740, and the needle cover 1330.

In some embodiments, the front housing 121 may be arranged to partially or completely accommodate one or more of the cushion 1710, the connection holder 1720, the syringe holder 1730, the safety spring 1740, and the needle cover 1330. In some embodiments, the needle cover 1330 may be arranged to partially or completely accommodate one or more of the cushion 1710, the connection holder 1720, the syringe holder 1730, and the safety spring 1740.

In some embodiments, one or more of the cushion 1710, the connection holder 1720, the syringe holder 1730, and the safety spring 1740 may partially or completely pass through the penetrable structure of the needle cover 1330. In some embodiments, the cushion 1710, the connection holder 1720, and the syringe holder 1730 may have a penetrable structure individually so that other components of the medical injection system 100 may be accommodated or passed therethrough. In some embodiments, one or more of the plunger 1430, the vial 1450, the needle guard 1460, and the case 1470 in the cartridge module 140 may partially or completely pass through the penetrable structure of the cushion 1710, the connection holder 1720, and the syringe holder 1730.

In some embodiments, one end of the two ends of the safety spring 1740 may contact the needle cover 1330 to drive the needle cover 1330 to move toward the distal end 101 of the medical injection system 100. In some embodiments, the other end of the two ends of the safety spring 1740 may contact the syringe holder 1730.

In some embodiments, the cushion 1710 may be detachably fixed to the connection holder 1720. In some embodiments, the cushion 1710 may further include one or more fixing protrusion 1711, and the connection holder 1720 may correspondingly further include one or more fixing holes 1721, wherein the fixing protrusions 1711 may be detachably coupled to the fixing holes 1721.

In some embodiments, the connection holder 1720 may be detachably fixed to the syringe holder 1730. In some embodiments, the connection holder 1720 may further include one or more fixing protrusions 1722, and the syringe holder 1730 may correspondingly further include one or more fixing holes 1732, wherein the fixing protrusions 1722 may be detachably coupled to the fixing holes 1732.

In some embodiments, the syringe holder 1730 may be detachably fixed to the front housing 121. In some embodiments, the syringe holder 1730 may further include one or more fixing protrusions 1731, and the front housing 121 may correspondingly further include one or more fixing holes 1211, wherein the fixing protrusions 1731 may be detachably coupled to the fixing holes 1211. In some embodiments, the needle cover 1330 may have one or more side openings so that the fixing protrusions 1731 of the syringe holder 1730 may protrude outward through the side openings. Therefore, when the needle cover 1330 moves toward the distal end 101 of the medical injection system 100, the movement range of the needle cover 1330 may be limited so that the needle cover 1330 would not be separated from the housing 120.

In some embodiments, further referring to FIG. 2, the syringe holder 1730 may be detachably coupled to the needle cover 1330. In some embodiments, the syringe holder 1730 may further include one or more elastic pieces 1733, and the needle cover 1330 may correspondingly further include one or more fixing holes 1332 and 1332', wherein the elastic pieces 1733 may be detachably coupled to the fixing holes 1332 and 1332'. In some embodiments, the elastic pieces 1733 of the syringe holder 1730 may be spring pieces arranged progressively away from the inner diameter of the syringe holder 1730 from the distal end 101 to the proximal end 102. In some embodiments, the fixing holes 1332 and 1332' of the needle cover 1330 may be elongated holes whose long sides are arranged along the longitudinal axis, and the elastic pieces 1733 of the syringe holder 1730 may pass through the elongated holes and contact the portion of the elongated holes near the proximal end 102 of the medical injection system 100 so as to limit the movement of the needle cover 1330 before the injection initiates. That is, the needle cover 1330 would not move toward the distal end 101 of the medical injection system 100.

In some embodiments, the syringe holder 1730 may further include one or more fixing pieces (not shown in the figures), which may be inverted grooves for accommodating the elastic pieces 1733 of the syringe holder 1730. In some embodiments, the needle cover 1330 may further include a buckle 1334 which may be disposed near the distal end 101 of the medical injection system 100. In some embodiments, the front housing 121 may further include one or more annular protrusions 1212 relative to the buckle 1334, which may be disposed on the inner wall near the distal end 101 of the medical injection system 100.

In some embodiments, the elastic pieces 1733 of the syringe holder 1730 may partially or completely pass through the fixing holes 1332 and 1332' of the needle cover 1330 when the elastic pieces 1733 are not subjected to an external force (e.g., not compressed inward by the needle cover 1330 or the fixing pieces). In some embodiments, when the user holds the housing 120 and presses the cartridge module 140 against the patient's skin, the movement of the needle cover 1330 toward the proximal end 102 of the medical injection system 100 may compress the elastic pieces 1733 of the syringe holder 1730 inward and cause the elastic pieces 1733 to be accommodated in the fixing pieces. Therefore, the elastic pieces 1733 of the syringe holder 1730 may be subjected to the inward external force of the fixing pieces and would no longer be expanded outward. When the user removes the cartridge module 140 from the patient's skin after the injection is completed, since movement of the needle cover 1330 is no longer limited by the elastic pieces 1733, the safety spring 1740 may drive the needle cover 1330 to move toward the distal end 101 of the medical injection system 100 to re-accommodate the needle body of the vial 1450. At this time, the buckle 1334 of the needle cover 1330 may be lower than the annular protrusions 1212 of the front housing 121 so that the position of the needle cover 1330 is closer to the distal end 101 of the medical injection system 100 than before the injection. In addition, since movement of the buckles 1334 is limited by the annular protrusions 1212, the needle cover 1330 may not move upward again. Therefore, the needle body may not be exposed again, thus improving the safety of use of the medical injection system 100.

Therefore, when the user intuitively presses the needle body of the injection system 100 of the present disclosure against the skin, the injection could be automatically triggered, and the prompts would be generated when the injection is started and completed, respectively, to improve the accuracy and convenience when the user self-administers a medical fluid or drug.

The embodiments shown and described above are only examples. Many details are often found in the art. Therefore, many such details are neither shown nor described herein. Even though numerous characteristics and advantages of the present disclosure have been set forth in the foregoing description, together with details of the structure and function of the present disclosure, the present disclosure is illustrative only, and changes may be made in the details. It will therefore be appreciated that the embodiment described above may be modified within the scope of the claims.

What is claimed is:

1. A medical injection system comprising:
an injection initiation feedback module comprising:
an actuator comprising an impact plate and one or more impact plate grooves on the impact plate; and
a click collar which forms a penetrable structure for accommodating the actuator, the penetrable structure of the click collar further comprising:
a click surface configured to correspond with the impact plate of the actuator; and
one or more click surface protrusions configured to resist the click surface from contacting the impact plate,
wherein, when the click collar is rotated to accommodate the one or more click surface protrusions in the one or more impact plate grooves, the click surface contacts the impact plate to generate an injection initiation feedback prompt.

2. The medical injection system of claim 1, further comprising:
an injection module comprising:
a starter having one end which contacts the click collar, wherein the click collar is driven to rotate when the starter rotates, and the starter forms a penetrable structure for accommodating the actuator, wherein the penetrable structure of the starter further comprises:
an inner annular surface; and
one or more accommodating spaces which are arranged on the inner annular surface to protrude outward, wherein the actuator further comprises:
one or more upper elastic pieces, and the inner annular surface presses the one or more upper elastic pieces inward,
wherein, when the starter rotates to accommodate the one or more upper elastic pieces of the actuator in the one or more accommodating spaces, the one or more click surface protrusions are simultaneously accommodated in the one or more impact plate grooves of the actuator.

3. The medical injection system of claim 2, wherein the click collar further comprises one or more rotational protrusions configured to contact the one end of the starter.

4. The medical injection system of claim 3, wherein another end of the starter comprises one or more rotational ramps; and
the injection module further comprises:
a needle cover comprising one or more motion steering protrusions contacting the one or more rotational ramps, and when the needle cover is moved in an axial direction of the medical injection system, the one or more motion steering protrusions push the one or more rotational ramps to cause the starter to rotate around an axis aligned with the axial direction and the click collar is driven to rotate.

5. The medical injection system of claim 4, further comprising:
a cartridge module comprising:
a plunger comprising a plunger recess corresponding to the one or more upper elastic pieces, wherein the plunger is configured to be accommodated in the actuator or the needle cover and move in another axial direction of the medical injection system;
wherein the actuator further comprises one or more rotating chutes, and when the one or more upper elastic pieces are compressed inward against the plunger recess, the actuator limits movement of the plunger in the other axial direction,
and wherein the penetrable structure of the starter further comprises:
one or more rotational protrusions located on the inner annular surface for rotating the starter by moving along the one or more rotating chutes, wherein the one or more upper elastic pieces are no longer compressed inward by the inner annular surface when the one or more accommodating spaces are rotated to align with the one or more upper elastic pieces.

6. The medical injection system of claim 5, wherein when the plunger moves in the other axial direction of the medical injection system, the click surface of the click collar contacts the impact plate of the actuator to generate the injection initiation feedback prompt.

7. The medical injection system of claim 5, further comprising a housing for accommodating the cartridge module and the injection module, wherein the actuator is fixed to the housing, and when the cartridge module is pressed down against skin of a subject, the needle cover is moved in the other axial direction of the medical injection system and the one or more motion steering protrusions push the one or more rotational ramps to cause the starter to rotate around an axis aligned with the axial direction.

8. The medical injection system of claim 5, further comprising an injection completion feedback module, wherein the injection completion feedback module comprises:
a click ring which forms a penetrable structure for accommodating the actuator; and a compression collar which forms a penetrable structure for accommodating the plunger, and an impact surface formed in the penetrable structure of the compression collar corresponding to the click ring, wherein when the click ring contacts the impact surface of the compression collar, an injection completion feedback prompt is generated.

9. The medical injection system of claim 5, further comprising a cap structure, wherein the cap structure comprises:

a cap cover which forms a structure accommodating at least a portion of the cartridge module; and a shield remover, which is arranged to be coupled to the cap cover and comprises a needle guard remover, wherein when the shield remover is removed from the medical injection system, the needle guard removers removes a needle guard to expose a needle body.

10. The medical injection system of claim 5, further comprising a backstop module, wherein the backstop module comprises:

a front housing which forms a structure accommodating at least a portion of the cartridge module and the injection module and comprises one or more fixing holes; and a syringe holder which is accommodated in the front housing and includes one or more fixing protrusions corresponding to the one or more fixing holes of the front housing to fix the syringe holder to the front housing, and the syringe holder further comprises one or more elastic pieces coupled to the needle cover to limit movement of the needle cover in the other axial direction of the medical injection system, wherein the syringe holder further comprises one or more fixing pieces corresponding to the one or more elastic pieces, and when the needle cover moves in the axial direction of the medical injection system, the one or more elastic pieces are compressed to be accommodated in the one or more fixing pieces, and the movement of the needle cover is no longer limited.

\* \* \* \* \*